US008427642B2

(12) United States Patent
Mitchell et al.

(10) Patent No.: US 8,427,642 B2
(45) Date of Patent: Apr. 23, 2013

(54) TWO-DIMENSIONAL OPTICAL IMAGING METHODS AND SYSTEMS FOR PARTICLE DETECTION

(75) Inventors: John Mitchell, Broomfield, CO (US); Jon Sandberg, Erie, CO (US); Karen R. Sandberg, legal representative, Shelton, WA (US); Dwight A. Sehler, Longmont, CO (US); Michael Williamson, Fayetteville, NY (US); David Rice, Syracuse, NY (US)

(73) Assignee: Particle Measuring Systems, Inc., Boulder, CO (US)

( * ) Notice: Subject to any disclaimer, the term of this patent is extended or adjusted under 35 U.S.C. 154(b) by 0 days.

(21) Appl. No.: 13/396,393

(22) Filed: Feb. 14, 2012

(65) Prior Publication Data

US 2012/0140223 A1    Jun. 7, 2012

Related U.S. Application Data

(63) Continuation of application No. 12/326,577, filed on Dec. 2, 2008, now Pat. No. 8,154,724.

(60) Provisional application No. 60/992,192, filed on Dec. 4, 2007, provisional application No. 61/005,336, filed on Dec. 4, 2007, provisional application No. 61/107,397, filed on Oct. 22, 2008.

(51) Int. Cl.
*G01N 21/00* (2006.01)

(52) U.S. Cl.
USPC ........................................... 356/343

(58) Field of Classification Search .... 356/243.1–243.8, 356/436–438
See application file for complete search history.

(56) References Cited

U.S. PATENT DOCUMENTS

| | | |
|---|---|---|
| 2,643,541 A | 6/1953 | McCreary |
| 3,200,373 A | 8/1965 | Rabinow |
| 3,303,466 A | 2/1967 | Holt |
| 3,406,289 A | 10/1968 | Schleusener |

(Continued)

FOREIGN PATENT DOCUMENTS

| | | |
|---|---|---|
| DE | 3338351 | 5/1984 |
| EP | 0 015 170 | 9/1980 |

(Continued)

OTHER PUBLICATIONS

Aikens (Nov. 1990) "Watch Out Photography, Here Come Cooled HCCD Cameras," *Photonics Spectra* :95-101.

(Continued)

*Primary Examiner* — Tara S Pajoohi Gomez
(74) *Attorney, Agent, or Firm* — Lathrop & Gage LLP

(57) ABSTRACT

The present invention provides methods and systems for particle detection and analysis using two-dimensional optical imaging to access enhanced detection sensitivity and expanded sensing functionality relative to conventional point and array detection-based optical particle counters. Methods and systems of the present invention provide a two-dimensional optical imaging-based particle sensing platform wherein system components and specifications are selected to generate reproducible and readily identifiable signals, including particle detection signatures, from optical scattering or emission from particles provided to the system. Systems and methods of the present invention are capable of accurately and sensitively detecting, identifying, and characterizing (e.g., determining the size of) particles in liquid phase or gas phase samples.

28 Claims, 26 Drawing Sheets

U.S. PATENT DOCUMENTS

| | | |
|---|---|---|
| 3,422,422 A | 1/1969 | Frank et al. |
| 3,534,289 A | 10/1970 | Clark et al. |
| 3,621,150 A | 11/1971 | Pappas |
| 3,634,823 A | 1/1972 | Dietrich et al. |
| 3,644,743 A | 2/1972 | Binek et al. |
| 3,669,542 A | 6/1972 | Capellaro |
| 3,700,333 A | 10/1972 | Charlson et al. |
| 3,705,771 A | 12/1972 | Friedman et al. |
| 3,718,868 A | 2/1973 | Pao et al. |
| 3,753,145 A | 8/1973 | Chesler |
| 3,758,787 A | 9/1973 | Sigrist |
| 3,766,489 A | 10/1973 | Rosenberg et al. |
| 3,770,351 A | 11/1973 | Wyatt |
| 3,797,937 A | 3/1974 | Shofner |
| 3,822,095 A | 7/1974 | Hirschfeld |
| 3,825,345 A | 7/1974 | Lorenz |
| 3,835,294 A | 9/1974 | Krohn et al. |
| 3,851,169 A | 11/1974 | Faxvog |
| 3,893,766 A | 7/1975 | Hogg |
| 3,899,748 A | 8/1975 | Bodlaj |
| 3,941,982 A | 3/1976 | Knollenberg et al. |
| 3,960,449 A | 6/1976 | Carleton et al. |
| 3,983,743 A | 10/1976 | Olin et al. |
| 4,074,939 A | 2/1978 | Rabl |
| 4,075,462 A | 2/1978 | Rowe |
| 4,110,043 A | 8/1978 | Eisert |
| 4,113,386 A | 9/1978 | Lepper |
| 4,173,415 A | 11/1979 | Wyatt |
| 4,178,103 A | 12/1979 | Wallace |
| 4,188,122 A | 2/1980 | Massie et al. |
| 4,243,318 A | 1/1981 | Stöhr |
| 4,272,193 A | 6/1981 | Eastman et al. |
| 4,273,443 A | 6/1981 | Hogg |
| 4,274,745 A | 6/1981 | Takahashi et al. |
| 4,281,924 A | 8/1981 | Aver et al. |
| 4,284,355 A | 8/1981 | Hansen et al. |
| 4,291,983 A | 9/1981 | Kraft et al. |
| 4,318,180 A | 3/1982 | Lundquist et al. |
| 4,329,054 A | 5/1982 | Bachalo |
| 4,338,024 A | 7/1982 | Bolz et al. |
| 4,348,111 A | 9/1982 | Goulas et al. |
| 4,361,400 A | 11/1982 | Gray et al. |
| 4,387,993 A | 6/1983 | Adrian |
| 4,411,525 A | 10/1983 | Ogawa |
| 4,429,995 A | 2/1984 | Goulas |
| 4,444,500 A | 4/1984 | Flinsenberg et al. |
| 4,496,839 A | 1/1985 | Bernstein et al. |
| 4,498,766 A | 2/1985 | Unterleitner |
| 4,522,494 A | 6/1985 | Bonner |
| 4,571,079 A | 2/1986 | Knollenberg |
| 4,573,796 A | 3/1986 | Martin et al. |
| 4,594,715 A | 6/1986 | Knollenberg |
| 4,596,464 A | 6/1986 | Hoffman et al. |
| 4,600,302 A | 7/1986 | Sage, Jr. |
| 4,609,286 A | 9/1986 | Sage, Jr. |
| 4,616,927 A | 10/1986 | Phillips et al. |
| 4,636,075 A | 1/1987 | Knollenberg |
| 4,653,056 A | 3/1987 | Baer et al. |
| 4,661,913 A | 4/1987 | Wu et al. |
| 4,662,742 A | 5/1987 | Chupp |
| 4,665,529 A | 5/1987 | Baer et al. |
| 4,673,820 A | 6/1987 | Kamen |
| 4,685,802 A | 8/1987 | Saito et al. |
| 4,693,602 A | 9/1987 | Wyatt et al. |
| 4,710,642 A | 12/1987 | McNeil |
| 4,723,257 A | 2/1988 | Baer et al. |
| 4,728,190 A | 3/1988 | Knollenberg |
| 4,737,025 A | 4/1988 | Steen |
| 4,739,177 A | 4/1988 | Borden |
| 4,739,507 A | 4/1988 | Byer et al. |
| 4,746,215 A | 5/1988 | Gross |
| 4,752,131 A | 6/1988 | Eisenlauer et al. |
| 4,753,530 A | 6/1988 | Knight et al. |
| 4,764,013 A | 8/1988 | Johnston |
| 4,781,459 A | 11/1988 | Suzuki |
| 4,786,165 A | 11/1988 | Yamamoto et al. |
| 4,798,465 A | 1/1989 | Knollenberg |
| 4,809,291 A | 2/1989 | Byer et al. |
| 4,814,868 A | 3/1989 | James |
| 4,830,494 A | 5/1989 | Ishikawa et al. |
| 4,850,707 A | 7/1989 | Bowen et al. |
| 4,872,177 A | 10/1989 | Baer et al. |
| 4,876,458 A | 10/1989 | Takeda et al. |
| 4,885,473 A | 12/1989 | Shofner et al. |
| 4,893,928 A | 1/1990 | Knollenberg |
| 4,896,048 A | 1/1990 | Borden |
| 4,917,496 A | 4/1990 | Sommer |
| 4,920,275 A | 4/1990 | Itoh |
| RE33,213 E | 5/1990 | Borden |
| 4,957,363 A | 9/1990 | Takeda et al. |
| 4,990,795 A | 2/1991 | Suzuki et al. |
| 4,992,190 A | 2/1991 | Shtarkman |
| 5,033,851 A | 7/1991 | Sommer |
| 5,033,852 A | 7/1991 | Zaglio |
| 5,067,814 A | 11/1991 | Suzuki et al. |
| 5,075,552 A | 12/1991 | McClelland et al. |
| 5,085,500 A | 2/1992 | Blesner |
| 5,090,808 A | 2/1992 | Ishikawa et al. |
| 5,092,675 A | 3/1992 | Sommer |
| 5,101,113 A | 3/1992 | Hirleman, Jr. et al. |
| 5,121,988 A | 6/1992 | Blesner et al. |
| 5,153,926 A | 10/1992 | Jansson et al. |
| 5,156,461 A | 10/1992 | Moslehi et al. |
| 5,159,397 A | 10/1992 | Kosaka et al. |
| 5,159,398 A | 10/1992 | Maekawa et al. |
| 5,262,841 A | 11/1993 | Blesener et al. |
| 5,282,151 A | 1/1994 | Knollenberg |
| 5,285,467 A | 2/1994 | Scheps |
| 5,329,351 A | 7/1994 | Clementi |
| RE34,729 E | 9/1994 | Sipes, Jr. |
| 5,370,842 A | 12/1994 | Miyazaki et al. |
| 5,396,333 A | 3/1995 | Aleshin et al. |
| 5,402,438 A | 3/1995 | Tanuma |
| 5,412,466 A | 5/1995 | Ogino |
| 5,428,451 A | 6/1995 | Lea et al. |
| 5,459,569 A | 10/1995 | Knollenberg et al. |
| 5,467,188 A | 11/1995 | Miyashita |
| 5,467,189 A | 11/1995 | Kreikebaum et al. |
| 5,471,515 A | 11/1995 | Fossum et al. |
| 5,475,487 A | 12/1995 | Mariella et al. |
| 5,481,357 A | 1/1996 | Ahsan et al. |
| 5,515,164 A | 5/1996 | Kreikebaum et al. |
| 5,565,984 A | 10/1996 | Girvin |
| 5,576,827 A | 11/1996 | Strickland et al. |
| 5,594,544 A | 1/1997 | Horiuchi et al. |
| 5,600,438 A | 2/1997 | Kreikebaum |
| 5,642,193 A | 6/1997 | Girvin et al. |
| 5,654,797 A | 8/1997 | Moreau et al. |
| 5,671,046 A | 9/1997 | Knowlton |
| 5,726,753 A | 3/1998 | Sandberg |
| 5,751,422 A | 5/1998 | Mitchell |
| 5,805,281 A | 9/1998 | Knowlton et al. |
| 5,825,487 A | 10/1998 | Felbinger et al. |
| 5,841,126 A | 11/1998 | Fossum et al. |
| 5,861,950 A | 1/1999 | Knowlton |
| 5,864,399 A | 1/1999 | Girvin et al. |
| 5,870,190 A | 2/1999 | Unger |
| 5,872,361 A | 2/1999 | Paoli et al. |
| 5,887,439 A | 3/1999 | Kotliar |
| 5,889,589 A | 3/1999 | Sandberg |
| 5,920,388 A | 7/1999 | Sandberg et al. |
| 5,946,092 A | 8/1999 | DeFreez et al. |
| 5,946,093 A | 8/1999 | DeFreeze et al. |
| 6,003,389 A | 12/1999 | Flagan et al. |
| 6,005,619 A | 12/1999 | Fossum |
| 6,016,194 A | 1/2000 | Girvin et al. |
| 6,067,157 A | 5/2000 | Altendorf |
| 6,091,494 A | 7/2000 | Kreikebaum |
| 6,104,491 A | 8/2000 | Trainer |
| 6,137,572 A | 10/2000 | DeFreeze et al. |
| 6,167,107 A | 12/2000 | Bates |
| 6,181,419 B1 | 1/2001 | Snelling et al. |
| 6,211,956 B1 | 4/2001 | Nicoli |
| 6,249,341 B1 | 6/2001 | Basiji et al. |
| 6,256,096 B1 | 7/2001 | Johnson |
| 6,275,288 B1 | 8/2001 | Atkinson et al. |
| 6,323,949 B1 | 11/2001 | Lading et al. |

| | | |
|---|---|---|
| 6,404,494 B1 | 6/2002 | Masonis et al. |
| 6,414,754 B1 | 7/2002 | Johnson |
| 6,465,802 B1 | 10/2002 | Matsuda |
| 6,628,386 B2 | 9/2003 | Davis et al. |
| 6,680,800 B1 | 1/2004 | Schreiber et al. |
| 6,710,878 B1 | 3/2004 | Dean et al. |
| 6,768,545 B2 | 7/2004 | Matsuda et al. |
| 6,784,981 B1 | 8/2004 | Roche et al. |
| 6,813,303 B2 | 11/2004 | Matsuda et al. |
| 6,859,277 B2 | 2/2005 | Wagner et al. |
| 6,903,818 B2 | 6/2005 | Cerni et al. |
| 6,906,792 B2 | 6/2005 | Ortyn et al. |
| 6,919,960 B2 | 7/2005 | Hansen et al. |
| 7,030,980 B1 | 4/2006 | Sehler et al. |
| 7,053,783 B2 | 5/2006 | Hamburger et al. |
| 7,075,647 B2 | 7/2006 | Christodoulou |
| 7,113,266 B1 | 9/2006 | Wells |
| 7,162,057 B1 | 1/2007 | Roth et al. |
| 7,170,601 B2 | 1/2007 | Matsuda |
| 7,221,453 B2 | 5/2007 | Sharpe et al. |
| 7,221,457 B2 | 5/2007 | Jorgenson et al. |
| 7,258,774 B2 | 8/2007 | Chou et al. |
| 7,456,960 B2 | 11/2008 | Cerni et al. |
| 7,518,723 B2 | 4/2009 | Adams et al. |
| 7,576,857 B2 | 8/2009 | Wagner |
| 7,916,293 B2 | 3/2011 | Mitchell et al. |
| 8,027,035 B2 | 9/2011 | Mitchell et al. |
| 2002/0057432 A1 | 5/2002 | Ortyn et al. |
| 2003/0016357 A1 | 1/2003 | Shofner et al. |
| 2003/0020910 A1 | 1/2003 | Peterson et al. |
| 2003/0112432 A1* | 6/2003 | Yguerabide et al. ......... 356/317 |
| 2004/0042008 A1 | 3/2004 | Wagner et al. |
| 2004/0067167 A1 | 4/2004 | Zhang et al. |
| 2004/0080747 A1 | 4/2004 | Cerni et al. |
| 2005/0024641 A1* | 2/2005 | DeFreez et al. ............... 356/343 |
| 2005/0030519 A1 | 2/2005 | Roth |
| 2005/0136548 A1 | 6/2005 | McDevitt et al. |
| 2006/0001874 A1 | 1/2006 | Matsuda |
| 2006/0038998 A1 | 2/2006 | Wagner |
| 2006/0221325 A1 | 10/2006 | Wells |
| 2006/0244965 A1 | 11/2006 | Ichijo |
| 2006/0274309 A1 | 12/2006 | Cerni et al. |
| 2007/0013910 A1 | 1/2007 | Jiang et al. |
| 2007/0146703 A1 | 6/2007 | Adams et al. |
| 2007/0146873 A1 | 6/2007 | Ortyn et al. |
| 2007/0165225 A1 | 7/2007 | Trainer |
| 2009/0190128 A1 | 7/2009 | Cerni |
| 2009/0219530 A1 | 9/2009 | Mitchell et al. |
| 2009/0244536 A1 | 10/2009 | Mitchell et al. |
| 2009/0268202 A1 | 10/2009 | Wagner |
| 2010/0225913 A1 | 9/2010 | Trainer |
| 2011/0155927 A1 | 6/2011 | Mitchell et al. |

FOREIGN PATENT DOCUMENTS

| | | |
|---|---|---|
| EP | 0300875 | 1/1989 |
| EP | 0 463 562 | 1/1992 |
| EP | 0 562 630 | 9/1993 |
| EP | 0 504 185 | 3/1994 |
| GB | 1497698 | 1/1978 |
| JP | 60-209147 | 10/1985 |
| JP | 63-11838 | 1/1988 |
| JP | 03148041 | 6/1991 |
| JP | 4-184241 | 7/1992 |
| JP | 4-289440 | 10/1992 |
| JP | 4-369464 | 12/1992 |
| JP | H06-026823 | 2/1994 |
| JP | 07-218419 | 8/1995 |
| JP | 9-113436 | 5/1997 |
| JP | 9-311103 | 12/1997 |
| JP | 10-2856 | 1/1998 |
| JP | 11-197868 | 7/1999 |
| JP | 11211650 | 8/1999 |
| JP | 2000-22265 | 1/2000 |
| JP | 2000-155087 | 6/2000 |
| JP | 2000-512390 | 9/2000 |
| JP | 2002-223019 | 8/2002 |
| JP | 3480669 | 12/2003 |
| JP | 2004-085573 | 3/2004 |
| JP | 2008-542761 | 11/2008 |
| WO | WO 90/10216 | 9/1990 |
| WO | WO 92/08120 | 5/1992 |
| WO | WO 99/02966 | 1/1999 |
| WO | WO 01/27686 | 4/2001 |
| WO | WO 02/29106 | 4/2002 |
| WO | WO 2004/031742 | 4/2004 |
| WO | WO 2005/095295 | 10/2005 |
| WO | WO 2005/100954 | 10/2005 |
| WO | WO 2006/067977 | 6/2006 |
| WO | WO 2006/132980 | 12/2006 |
| WO | WO 2007/029480 | 3/2007 |
| WO | 2009/073649 | 6/2009 |
| WO | WO 2009/073649 | 6/2009 |
| WO | WO 2009/073652 | 6/2009 |

OTHER PUBLICATIONS

Altmann et al. (Mar. 15, 1981) "Two-Mirror Multipass Absorption Cell," *Applied Optics* 20(6):995-999.

Amnis (2004) "Time Delay Integration: Enabling High Sensitivity Detection for Imaging-in-Flow on the Image Stream® 100 Cell Analysis System," http://dp.univr.it/~laudanna/Systems%20Biology/Technologies/ImageStream/Tech%20Notes/Technology%20Report%20Time%20Delay%20Integration.pdf.

Arashiki, S. (Oct. 1999) "Detection Principle and Performance of the Liquid-Borne Particle Counters," *RION Technical Notes* 616-2: 6 pages.

Borso, C.S. (1982) "Optimization of Monolithic Solid State Array Detectors for the Positionin Encoding of Small Angle X-Ray Scattering from Synchrotron Sources," *Nuc. Instrom. Meth.* 204:65-72.

British Search Report, Corresponding to Great British Application No. GB 0318240.9, Completed Dec. 15, 2003.

Cerni, T.A. (2001) "High Sensitivity, High Sample Rate, Aerosol Optical Particle Counter," *Clean Technol.* 11(6):12-14.

Dalsa (2005) "CCD vs. CMOS," http://www.dalsa.com/corp/markets/CCD_vs_CMOS.aspx.

Faxvog (Oct. 1976) "New Laser Particle Sizing Instrument," Research Publication GMR-2263, Research Laboratories, General Motors Corporation, Warren Michigan.

Herriott et al. (Aug. 1965) "Folded Optical Delay Lines," *Applied Optics* 4(8):883-889.

Herriott et al. (Apr. 1964) "Off-Axis Paths in Spherical Mirror Interferometers," *Applied Optics* 3(4):523-526.

International Search Report and Written Opinion Corresponding to International Application No. PCT/US2008/085243, Mailed Jan. 30, 2009.

International Search Report and Written Opinion, Corresponding to International Application No. PCT/US2008/085236, Mailed Feb. 5, 2009.

International Search Report and Written Opinion Corresponding to International Application No. PCT/US2006/021483, Mailed Feb. 11, 2006.

Japanese Official Action, Corresponding to Japanese Application No. 2003-303709, Mailed Mar. 31, 2009.

Japanese Official Action, Corresponding to Japanese Application No. 2003-303709, Mailed Feb. 2, 2010.

Knollenberg et al. (Jan. 1987) "In Situ Optical Particle Size Measurements in Liquid Media," Proceedings of Pure Water Conference, Palo Alto California, Jan. 13-14.

Knollenberg, R.G. (Jan./Feb. 1985) "The Measurement of Particle Sizes below 0.1 Micrometers," *J. Environ. Sci.* :32-51.

Knowlton, D.K. (1998) "Inviscid Jet Technology for Monitoring Particles in Fluids," *Proceedings 1998 Institute of Environmental Sciences and Technology* pp. 34-39.

Liu et al. (Apr. 2000) "CMOS Uncooled Heat-Balancing Infrared Imager," *IEEE J. Solid-State Circuits* :1-9.

Micron (Jan. 2004) "1.3-Megapixel CMOS Active-Pixel Digital Image Sensor," Micron Document No. Mt0M43C365TC.fm—Ver. 3.0, http://www.micron.com/products/imaging/products/MT9M413.html.

Notice of Reasons for Rejection dated May 29, 2012, for Japanese Patent Application No. P2010-537012.

First Office Action corresponding to Chinese Patent Application No. 200880125744.9, dated Mar. 7, 2012 (includes English translation).

Knollenberg, R.G. (1987) "Sizing Particles at High Sensitivity in High Molecular Scattering Environments," *Proc Int. Environ. Sci.* :428-435.

Knollenberg, R.G. (1992) "The Design of a High Sensitivity Large Sample Volume Particle Counter for Ultra Clean DI Water," *Microcontamination 92 Conference Proceedings*, Santa Clara, CA, pp. 764-776.

Knollenberg et al. (1991) "Optical Particle Monitors, Counters and Spectrometers: Performance, Characterization, Comparison and Use," *Proceedings of the Institute of Environmental Sciences Conference*, San Diego, California, pp. 751-771.

Knowlton, D.K. (1998) "Inviscid Jet Technology for Monitoring Particles in Fluids," *Proceedings 1998 Institute of Enviornmental Sciences and Technology* pp.34-99.

Liu et al. (Apr. 2000) "CMOS Uncooled Heat-Balancing Infrared Imager," *IEEE J. Solid-State Circuits*:1-9.

Micron (Jan. 2004) "1.3-Megapixel CMOS Active-Pixel Digital Image Sensor," Micron Document No. Mt0M43C365TC.fm — Ver. 3.0, http://www.micron.com/products/imaging/products/MT9M413.html.

Office Action Corresponding to U.S. Appl. No. 12/326,335, Mailed Oct. 7, 2010.

Rion "Particle Counter KS-41 for photoresist measurement," www.mgnintl.com/pdf/LPC for Resist e.ppt ; Jun. 24, 1998.

Rion "Liquid-Borne Particle Counter for Pure Water Model XP-L4," Technical Information, Tokyo Japan; Jan. 15, 1999.

Schuster et al. (Jul. 1972) "Detection and Sizing of Small Particles in an Open Cavity Gas Laser," *Appl. Opt.* 11(7):1515-1520.

Tezcan et al. (Feb. 2003) "A Low-Cost Uncooled Infrared Microbolometer Detector in Standard CMOS Technology," *IEEE Trans. Electron Dev.* 50(2):494-502.

Titus, H. (Feb. 2001) "Imaging Sensors that Capture your Attention," *Sensors* 18(2).

Ueki et al. (Jul. 1992) "Semiconductor Laser 2-Focus Velocimeter and the Application Thereof," The $29^{th}$ Lecture Meeting of Turbomachinery Society in Toyama, Japan, Turbomachinery Society, pp. 241-244.

Ueki et al. (Dec. 25, 1992) "Flow Velocimeter with Wide-Stripe Semiconductor Laser," *Collection of Papers of the Japan Society of Mechanical Engineers* 58(556):171-175.

von Freyhold et al. (Nov. 2002) "Powerful Laser Diodes Become High-Brightness Laser Tools," *Photonics Showcase* pp. 5-6.

* cited by examiner

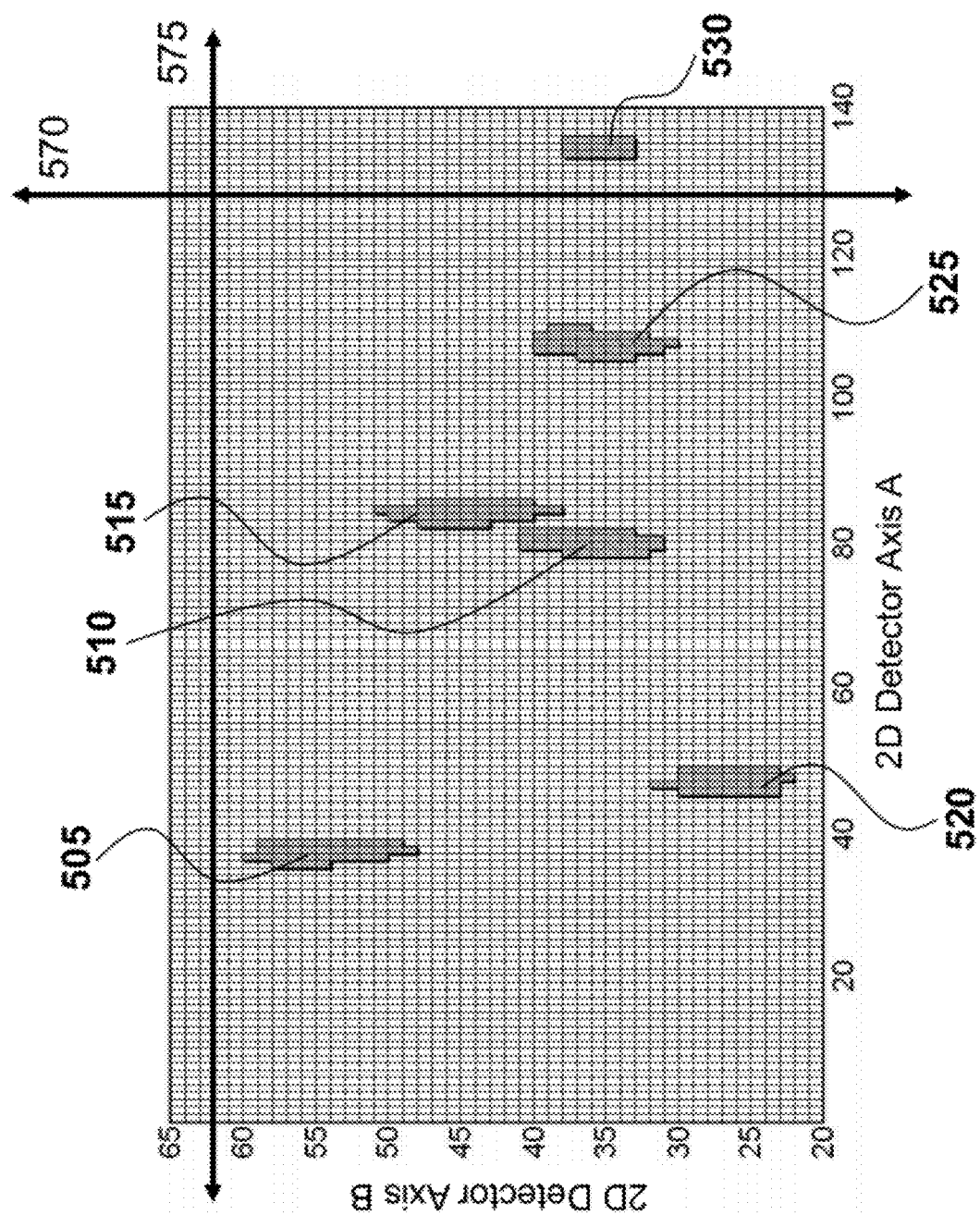

US 8,427,642 B2

TWO-DIMENSIONAL OPTICAL IMAGING METHODS AND SYSTEMS FOR PARTICLE DETECTION

CROSS-REFERENCE TO RELATED APPLICATIONS

This application is a continuation of U.S. patent application Ser. No. 12/326,577, filed on Dec. 2, 2008, which claims the benefit of U.S. Provisional Patent Application Nos. 60/992,192, 61/005,336, and 61/107,397 filed on Dec. 4, 2007, Dec. 4, 2007 and Oct. 22, 2008, respectively, each of which are hereby incorporated by reference in their entireties to the extent not inconsistent with the present description.

STATEMENT REGARDING FEDERALLY SPONSORED RESEARCH OR DEVELOPMENT

Not applicable.

BACKGROUND OF INVENTION

This invention is in the field of optical particle analyzers. This invention relates generally to two-dimensional optical imaging-based methods and systems for detecting and characterizing particles in fluid samples. This invention also relates generally to methods and systems for improving the sensitivity and versatility of optical particle analyzers and for extending device performance of these systems so as to accurately detect and characterize particles having small physical dimensions (e.g., less than 0.1 microns).

A large portion of the micro-contamination industry and clean manufacturing industries is reliant on the use of optical particle counters, such as are described in a large number of U.S. patents, including U.S. Pat. Nos. 3,851,169, 4,348,111, 4,957,363, 5,085,500, 5,121,988, 5,467,188, 5,642,193, 5,864,399, 5,920,388, 5,946,092, and 7,053,783. Particle counters are also described in U.S. Pat. Nos. 4,728,190, 6,859,277, and 7,030,980, 5,282,151, which are hereby incorporated by reference in their entirety.

Optical particle sensors and counters are useful in a variety of industrial applications including in semiconductor, pharmaceutical and microelectronics industries. In some industrial settings, optical particle sensors and counters provide an important tool for continuously monitoring the composition and purity of materials used in a process, for example, in the production of pharmaceutical products subject to stringent regulatory requirements relating to particulate contaminates. In other industrial settings, optical particle sensors and counters provide an important tool for providing quality control analysis, for example for off-line quality control checking of high quality photoresist and semiconductor materials. It is particularly advantageous to rapidly identify when a fluid is contaminated with unwanted particles so that the process can be stopped at an early stage, thereby avoiding wasteful manufacture of defective product. For example, in semi-conductor and other clean-room settings, or industries requiring sterile and pure production (e.g., pharmaceuticals), material fluids that are used to make the end products are continuously monitored to ensure adequate purity and that any unwanted particles suspended in the fluid is within an acceptable tolerance range. Aerosol particle counters are often used to measure air-born particle contamination in clean-rooms and clean zones. Liquid phase particle counters are often used to measure particulate contamination in pharmaceutical, water treatment and chemical processing industries.

The importance of particle monitoring sensors is reflected in the continuous and ongoing improvement and development of these devices to improve reliability and throughput, and to enable detection and characterization of particles having smaller sizes. In addition to limitations on sensitivity and particle sizing capability, state of the art optical particle counters are currently susceptible to problems relating to false counts generated when detector noise and/or signals resulting from processes other than optical scattering from particles are attributed to a particle detection event. The occurrence of false counts adversely impacts accuracy and sensitivity of the systems. Furthermore, the occurrence of false counts also impedes the capability of optical particle analyzers to accurately detect and characterize particles having small physical dimensions (e.g., less than 0.1 microns). As a result, design strategies for avoiding or suppressing false counts in optical particle counters and analyzers is recognized as a priority in development of the next generation of these devices.

SUMMARY OF THE INVENTION

The present invention provides methods and systems for particle detection and analysis using two-dimensional optical imaging to access enhanced detection sensitivity and expanded sensing functionality relative to conventional point-based and array-based optical particle counters. Methods and systems of the present invention provide a two-dimensional optical imaging-based particle sensing platform wherein system components and specifications are selected to generate reproducible and readily identifiable signals, including particle detection signatures, from optical scattering or emission from particles provided to the system. Systems and methods of the present invention are capable of accurately and sensitively detecting, identifying, and characterizing (e.g., determining the size of) particles in liquid phase or gas phase environments. Systems and methods of the present invention are capable of efficiently generating and identifying particle detection signatures in real time, thereby enabling analysis and filtering of output data from a two-dimensional detector configured for imaging electromagnetic radiation scattered or emitted by particles.

In an aspect, two-dimensional optical imaging methods and systems of the present invention are capable of generating distinctive particle detection signatures comprising well defined one- or two-dimensional patterns of output signals from a plurality of detector elements provided in an array of a two dimensional detector. Generation of distinctive particle detection signatures is used in the present invention to distinguish optical scattering or emission from particles from molecular scattering from the background fluid, detector noise, and/or detector signals arising from processes other than the interaction of electromagnetic radiation with particles of interest. Particle detection based on identification and characterization of distinctive particle detection signatures of this aspect of the present invention provides a number of performance benefits for particle counting and sizing applications. First, particle detection via identification and characterization of distinctive particle detection signatures significantly suppresses false counts from detector signals arising from sources other than the particle scattering or emission of events of interest, such as high energy photons (e.g., cosmic rays), detector noise and scattering or emission from non-particle sources. Decreasing false counts improves the accuracy of the present particle detection, counting and sizing measurements and systems relative to the conventional particle analyzers. Second, use of threshold dependent particle detection signatures enables detection and characterization of particles with smaller physical dimensions while simultaneously avoiding false counts resulting from non-particle noise sources.

In an embodiment, the present invention provides methods for detecting and/or characterizing particles in a sample by generating and identifying a particle detection signature using two-dimensional optical detection or imaging. In a specific embodiment, the present invention provides a method for detecting a particle(s) in a fluid flow comprising the steps: (i) providing the fluid flow having the particle(s), optionally characterized by a selected flow direction; (ii) exposing the fluid flow to a beam of electromagnetic radiation, wherein interaction between the particle(s) and the beam generates scattered or emitted electromagnetic radiation; (iii) directing at least a portion of the scattered or emitted electromagnetic radiation onto a plurality of detector elements provided in an array of a two-dimensional detector, (iv) detecting at least a portion of the scattered or emitted electromagnetic radiation directed onto the plurality of detector elements, wherein at least a portion of the detector elements of the array generate output signals corresponding to intensities of the scattered or emitted electromagnetic radiation; (v) measuring output signals for at least a portion of the detector elements of the array; and (vi) identifying a particle detection signature comprising a pattern of a plurality of output signals of detector elements each having an output signal greater than or equal to a threshold value for a given detector element; thereby detecting the particle in the fluid flow. In an embodiment, the method of this aspect further comprises the step of imaging at least a portion of the scattered or emitted electromagnetic radiation onto the detector elements of the array, and in some embodiments, at least a portion of the detector elements of the array generate output signals corresponding to intensities of the scattered and/or emitted electromagnetic radiation and background scattered electromagnetic radiation. Particle detection signatures of this aspect have distinct and reproducible features, such as shapes, number of detected elements, including number of directly adjacent detector elements, and/or distributions of output signals (e.g., intensity values) that can be readily identified and distinguished from molecular scattering from the background fluid, detector noise, and detector signals resulting from processes other than particle scattering or emission (e.g., interaction with cosmic rays, etc.). In an embodiment, the method of the present invention further comprises the step of analyzing the particle detection signature to provide an indication or measurement of a characteristic of the particle such as the size, shape and/or physical dimensions (e.g., diameter, radius, thickness, length, width, aerodynamic diameter, etc.) of the particle.

As will be appreciated by one skilled in the art, the methods and system of the present invention do not require collection or detection of all of, or even a majority of, the electromagnetic radiation scattered or emitted from particles. Detection of a portion, even a small portion, of the electromagnetic radiation scattered or emitted by the particles of interest is sufficient to practice the methods of the present invention. For example, detection of a sufficient amount of electromagnetic radiation scattered or emitted from the particles of the present invention includes detection of an amount of electromagnetic radiation which has intensity substantially greater than that of the background electromagnetic radiation level directed or imaged onto the two-dimensional detector of the present invention.

In the context of this description, an "output signal" refers to the signal of an individual detector element of a detector array of a two-dimensional detector, such as signal from a detector element corresponding to an intensity value of detected electromagnetic radiation. Output signals include time averaged detector element output signals, integrated detector element output signals, output signals having a background component subtracted and output signals subject to other signal processing (e.g., data smoothing, etc.). In an embodiment, for example, each of the output signals have a background value that is subtracted.

In many instances, the background value subtracted from an output signal varies from detector element-to-detector element in the two-dimensional array. As used herein, the expression "background value" or simply "background" refers to the output signal(s) of a detector element under detection conditions in the absence of electromagnetic radiation scattered and/or emitted from a particle of interest. Such detection conditions corresponding to the background value include: (i) detection conditions wherein no particle of interest interacts with the beam of electromagnetic radiation and/or (ii) detection conditions wherein a particle does interact with the beam of electromagnetic radiation but the position of the detector element in the array is such that the detector element does not detect scattered and/or emitted electromagnetic radiation from the particle. The expression "background value" and "background" includes an average output signal value, median output signal value or mean output signal value corresponding to a plurality of output signal(s) of a detector element for detection conditions in the absence of electromagnetic radiation scattered and/or emitted from a particle of interest, for example an average, median or mean value corresponding to 20 to 1000 output signal measurements under such detection conditions, and in some embodiments corresponding to 200 to 500 output signal measurements under such detection conditions. For example, a background value in some embodiments corresponds to an average of 20 to 200 intensity measurements for detection conditions in the absence of electromagnetic radiation scattered and/or emitted from a particle of interest, and therefore may be regarded as the "steady state" intensity value for an individual detector element.

In some embodiments, the background value subtracted from an output signal varies with the position of a detector element in the array and/or other experimental conditions (e.g., intensity and beam profile of the optical source, composition of the fluid etc.). In some embodiments, the background values subtracted from output signals are continuously updated during particle analysis. For example background values are continuously updated in an embodiment by measurement and processing of output signals from detector elements that do not received scattered or emitted electromagnetic radiation arising from a particle detection event. As will be understood by those having skill in the art, even during a particle detection event only a small portion of the detector element may receive and detect scattered or emitted electromagnetic radiation from the particle, thereby allowing background values of other detector elements in the array to be continually updated in certain methods and system of the present invention.

Particle detection signatures comprise a pattern of a plurality of output signals from individual detector elements (e.g., pixel elements of a two-dimensional array detector) that meet a criterion of having an output value that is larger than a threshold value preselected for a given detector element in the array. Output signals from detector elements of the array that do not meet this threshold dependent criterion are, therefore, not components of the pattern of output signals making up the particle detection signature. In this manner, the particle detection signatures of methods and systems of the present invention are referred to as threshold dependent and the expression "above-threshold" refers specifically to detector elements having output signal values that exceed the threshold value. In some embodiments of the present invention, threshold values for individual detector elements of the array are the same. The invention includes embodiments, however, wherein at least some of the threshold values for individual detector elements of the array are different. The invention includes methods and systems, for example, wherein threshold values vary with the position of a given detector element in the array. For example, in an embodiment, threshold values are derived from actual noise measurements corresponding to individual detector elements of the array (e.g., pixels of a two-dimensional detector). Such noise measurements commonly vary from detector element-to-detector element due to the spatial inhomogeneity intensity profile of the optical source (e.g., laser), the geometry of the optical cell, and optical properties of the optical elements in the system (e.g., lenses, windows, etc.) among other factors. Threshold values of the present invention may vary with system parameters such as intensity of the beam of electromagnetic radiation and/or detector gain.

The present invention includes methods and systems wherein the threshold value for a given detector element is derived from measurements of the noise for a given detector element in the array and/or measurements of the output signal values for a given detector element in the array in the absence of electromagnetic radiation scattered or emitted by a particle of interest (e.g., measured background values). Use of threshold values greater than the standard deviation of measured noise levels for a given detector element or greater than the standard deviation of the measured background values for a given detector element is useful for distinguishing a particle detection event from molecular scattering from the background fluid, detector noise, or detector signals resulting from processes other than scattering or emission from a particle and is also useful for detecting particles having very small physical dimensions (e.g, diameter less than 100 nanometers). In an embodiment, for example, the threshold value for a given detector element in the array is equal to or greater than 2.5 times the standard deviation of the noise of the detector element or equal to or greater than 2.5 times the standard deviation of output signals for the detector element for detection conditions in the absence of scattered or emitted electromagnetic radiation from a particle of interest (e.g., the background values for the detector element). Optionally for some embodiments, the threshold value for a given detector element is equal to or greater 3 times the standard deviation of the noise of the detector element or is equal to or greater 3 times the standard deviation of output signals for the detector element for detection conditions in the absence of scattered or emitted electromagnetic radiation from a particle of interest (e.g., the background values for the detector element). Optionally for some embodiments, the threshold value for a given detector element is equal to or greater 5 times the standard deviation of the noise of the detector element or is equal to or greater 5 times the standard deviation of output signals for the detector element for detection conditions in the absence of scattered or emitted electromagnetic radiation from a particle of interest (e.g., the background values for the detector element). In an embodiment, for example, the threshold value for a given detector element is equal to 2.5 to 7 times the standard deviation of the noise of the detector element or 2.5 to 7 times the standard deviation of output signals for the detector element for detection conditions in the absence of scattered or emitted electromagnetic radiation from a particle of interest (e.g., the background values for the detector element), and optionally for some embodiments the threshold value for a given detector element is equal to 2.5 to 5 times the standard deviation of the noise of the detector element or 2.5 to 5 times standard deviation of output signals for the detector element for detection conditions in the absence of scattered or emitted electromagnetic radiation from a particle of interest (e.g., the background values for the detector element).

In some methods and systems of the invention, threshold values are determined empirically, for example, by measuring output signal values for detection conditions in the absence of scattered or emitted electromagnetic radiation from a particle of interest (e.g, a background value) for a given detector element as a function of time and calculating the noise for an individual detector element in the array. As used herein, the expression "noise level" or simply "noise" refers to the difference between output signals of the detector element for detection conditions in the absence of electromagnetic radiation scattered and/or emitted from a particle of interest and an average background value, median background value or mean background value for the detector element. In some embodiments, therefore, noise or noise level is a measurement of the variation of a series of measurements of the background value for a given detector element in the array. The noise of individual detector elements of the two dimensional detector can be determined by measuring the background values of a detector element as a function of time. As used herein, standard deviation refers to the root-mean-square (RMS) deviation of the measured parameter (e.g., noise, background value, or output signal in absence of scattered or emitted radiation from a particle, etc.) from its mean value, or refers to the square root of the variance of the measured parameter. In an embodiment, for example, the standard deviation ($\sigma$) is determined using the expression:

$$\sigma = \sqrt{\frac{1}{N}\sum_{i=1}^{N}(x_i - \bar{x})^2}, \quad (I)$$

wherein N is the number of noise measurements, background value or other output signal values measured for a given detector element, $x_i$ refers to individual noise measurements, background values or other output signal values measured for a given detector element, and $\bar{x}$ is the arithmetic mean of the measured noise measurements, background values or output signal values for a given detector element. Alternatively, threshold values are determined theoretically in some embodiments, for example using ab initio methods for predicting/characterizing detector noise and other detector attributes.

Particle detection signatures of the present invention are characterized by a geometric component that corresponds to the shape, longitudinal dimensions and/or lateral dimensions in one or two spatial dimensions of the pattern of output signals comprising the particle detection signature. As used in this context, the geometric shape includes a one-dimensional or two-dimensional spatial distribution of the pattern of output signals comprising the particle detection signature. Output signals of the geometric signature are each individually addressed to specific detector elements having well defined positions in the detector array. Accordingly, in the context of this description, the spatial distribution or shape of the pattern of output signals refers to the spatial distribution or shape of detector elements for which the output signals of the particle detection signature are individually addressed. Geometric shape, in some embodiments, has a longitudinal component corresponding to a series of neighboring or directly neighboring detector elements provided along a longitudinal dimension of the particle detection signature, and/or a lateral component corresponding to a series of neighboring or directly neighboring detector elements provided along a lateral dimension of the particle detection signature. In an embodiment, for example, the particle detection signature has a geometric shape characterized by above-threshold output signal values from 3 or more longitudinally adjacent, directly neighboring detector elements, and in some embodiments has a geometric shape characterized by output signal values from 5 or more longitudinally adjacent, directly neighboring detector elements. In an embodiment, for example, the particle detection signature has a geometric shape characterized by above-threshold output signal values from 2 or more laterally adjacent, directly neighboring detector elements, and in some embodiments has a geometric shape characterized by output signal values from 4 or more laterally adjacent, directly neighboring detector elements.

The intensity values for detector pixel elements often depends on, in part, specific characteristics of a particle such as the optical properties, physical dimensions and/or flow velocity of sample passing through the beam of electromagnetic radiation, as well as the specific design and operation parameters of the particle detection system, including the physical dimensions, intensity distribution and shape of the beam of electromagnetic radiation, and the design of the optics for directing at least a portion of the electromagnetic radiation onto the detector array. In contrast, the geometric shape of a particle detection signature is often times largely independent of particle size or shape. Therefore, the shape of a measured particle detection signature is used in the present invention to distinguish detector array output signals corresponding to scattering or emission from a particle detection event from molecular scattering from the background fluid, detector noise, or detector signals arising from processes other than optical scattering or emission from a particle. Analysis of the intensity values of pixels corresponding to a particle detection signature is also useful in the present methods and systems for providing a measurement of the size, physical dimensions and number of particles passing through the beam of electromagnetic radiation. The present invention includes use of particle detection signatures having a range of shapes including rectangular, ellipsoidal, circular, square, triangular or any combination of these shapes.

In an embodiment useful for suppressing the occurrence of false counts and for detecting particles having small (e.g., less than 10 microns) physical dimensions, the methods and systems of the present invention generate a particle detection signature having an elongated shape, such as a substantially rectangular shape. The elongated nature of particle detection signatures of this aspect results, at least in part, from scattering processes occurring as a particle is physically transported (e.g., transported in a fluid flow) through the beam of electromagnetic radiation. The longitudinal dimension of an elongated particle detection signature, therefore, corresponds, at least in part, to the flow direction and trajectory of the particle(s) passing through the beam. The present invention includes embodiments wherein the flow rate and trajectory of particles transported through the beam are well defined parameters, so as to generate an elongated particle detection signature, such as a substantially rectangular particle detection signature, having well defined, reproducible longitudinal dimensions as a function of particle size, such as at least 3 above-threshold output signals from longitudinally adjacent, directly neighboring detector elements. A method of the present invention comprises determining a number of detector elements for a longitudinal component of a geometric signature corresponding to an elongated dimension.

In some embodiments, methods and systems of the present invention generate particle detection signatures comprising a pattern of a plurality of output signals from neighboring detector elements of the array, including directly neighboring detector elements. In the context of this description, the expression "neighboring" refers to detector elements positioned within 5 detector elements of each other, and the expression "directly neighboring detector elements" refers to detector elements positioned directly adjacent to each other in the array. Neighboring and directly neighboring detector elements may be longitudinally adjacent or laterally adjacent. In an embodiment, the particle detection signature comprises output signals from at least 2 neighboring detector elements, and in some embodiments, at least 2 directly neighboring detector elements. In an embodiment, the particle detection signature comprises output signals from between 2 and 20 neighboring detector elements, and in some embodiments, between 2 and 20 directly neighboring detector elements. In an embodiment, the particle detection signature comprises output signals from between 2 and 7 neighboring detector elements, and in some embodiments, between 2 and 7 directly neighboring detector elements.

The geometric shape of particle detection signatures useful for some embodiments may be further characterized in terms of a longitudinal component and/or lateral component. As used herein, a "longitudinal component" or "lateral component" of a particle detection signature corresponds to a plurality of adjacent, optionally directly adjacent, detector elements having output signals greater than or equal to a threshold value given detector elements that are positioned adjacent to each other along a selected axis or dimension of the particle detection signature, such as a longitudinal dimension or axis, or a lateral dimension or axis. For example, useful particle detection signatures of the present invention include a pattern of, detector elements that comprise a series of directly neighboring detector elements extending along a longitudinal dimension or lateral dimension of the particle detection signature.

In an embodiment, the shape of the pattern of output signals of the particle detection signature has a longitudinal component corresponding to a series of adjacent or directly adjacent detector elements having output signals greater than or equal to a threshold value for a given detector element that are positioned along a longitudinal dimension of the particle detection signature. In some embodiments of this aspect the longitudinal component corresponds to a distribution of intensities of the scattered or emitted electromagnetic radiation along the flow direction of the fluid. In an embodiment preferred for some applications, for example, the longitudinal component comprises above-threshold output signals from between 2 and 20 neighboring detector elements, optionally between 2 and 20 directly neighboring detector elements. In an embodiment, the pattern of output signals of the particle detection signature has a lateral component oriented orthogonal to the longitudinal component. In an embodiment preferred for some applications, for example, the lateral component comprises above-threshold output signals from between 2 and 10 neighboring detector elements, optionally between 2 and 10 directly neighboring detector elements.

Particle detection signatures of some methods and systems of the present invention are characterized by a one-dimensional or two-dimensional spatial distribution of output signal values, such as output signal values corresponding to the intensity of scattered or emitted electromagnetic radiation received by individual detector elements of the array, that meet the threshold criteria for the particle detection signature. Such intensity distributions of a particle detection signature may be analyzed in the present methods and systems to provide a determination or measurement of a characteristic of a particle, such as the size, shape and/or physical dimensions (diameter, radius, thickness, length, width, aerodynamic diameter, etc.) of a particle. Intensity distributions of a measured particle detection signature may also be used in the present invention to distinguish detector array output signals corresponding to scattering or emission from a particle of interest from molecular scattering from the background fluid, detector noise, or detector signals arising from processes other than optical scattering or emission from a particle. Analysis of a intensity distribution component (e.g., one- or two dimensional intensity distribution) can be carried out via a number of analytic techniques in the present invention including, but not limited to, pattern recognition analysis, image threshold analysis and/or image shape analysis. In an embodiment, the particle detection signature is analyzed by calculation of an average value of the output signals of the detection signature or a portion of the signature, such as a portion encompassing a maximum output signal of the detection signature. In an embodiment, the particle detection signature is analyzed by calculation of an integrated intensity value of the output signals of the detection signature or a portion of the signature, such as a portion encompassing a maximum intensity value of the output signals of the detection signature. In an embodiment, the particle detection signature is analyzed by determining the weighted center of intensity of the output signals of the detection signature or a portion of the signature, and optionally determining the output signal of the detector element corresponding to the weighted center of intensity or determining an average intensity corresponding to a distribution of output signals surrounding and including the output signal of the detector element corresponding to the weighted center of intensity. In an embodiment, the particle detection signature is analyzed by determination of the size, shape and/or number of detector elements corresponding to the detection signature.

In an embodiment, particles are detected by identifying a particle detection signature having at least 3 longitudinally adjacent, directly neighboring detector elements, and in some embodiments from 3-100 longitudinally adjacent, directly neighboring detector elements. In this aspect, identification of the particle detection signature provides a means of effectively identifying a particle detection event, thereby enabling particles to be counted and analyzed for example with respect to size. In some embodiments, a characteristic of the detected particle, such as particle size, is subsequently determined by analysis of the particle detection signature. In an embodiment, for example, the analysis comprises the step of determining the largest output signal value of the particle detection signature. In an embodiment, for example, the analysis comprises the step of determining an average output signal value of the output signals comprising the particle detection signature. In an embodiment, for example, the analysis comprises the step of determining an integrated output signal value of at least a portion of, and in some embodiments all of, the output signals comprising the particle detection signature. In an embodiment, for example, the analysis comprises determining the weighted center of the output signal values of at least a portion of, and in some embodiments all of, the output signals comprising the particle detection signature. Optionally, methods and systems of this aspect further comprise indentifying an output signal value and/or detector element corresponding to the output signal corresponding to the weighted center. Optionally, methods and systems of this aspect further comprise indentifying an average output signal value and/or an integrated output signal value corresponding to a plurality of output signals corresponding to adjacent, directly neighboring detector elements that include the weighted center, for example, a plurality of output signals from adjacent, directly neighboring detector elements that surround the weighted center. In an embodiment, for example, the analysis step comprises determining an integrated output signal value corresponding to 10 or more output signal values that surround the weighted center, or optionally corresponding to 20 or more output signal values that surround the weighted center. In an embodiment, for example, the analysis step comprises determining an integrated output signal value or average output signal value corresponding to output signal values surrounding the weighted center corresponding to an array of adjacent, directly neighboring detector elements characterized by an array of 3-10 columns by 7-15 rows of detector elements in the array. In methods of this aspect, an output signal value, an average output signal value, an integrated output signal value or any combination of these is used to determine the size of the particle, for example, using an algorithm, table of empirically or calculated reference values, or other correlation that relates an output signal value, an average output signal value, an integrated output signal value to particle size. The present invention includes methods and systems wherein the analysis of a particle detection signature is achieved by carrying out a plurality of the steps, processes and techniques as described above.

In an embodiment, a method of the present invention further comprises the steps of: (i) providing a fluid flow having a reference particle of a predetermined size; (ii) exposing the fluid flow having the reference particle to a beam of electromagnetic radiation, wherein interaction between the reference particle and the beam generates scattered or emitted electromagnetic radiation from the reference particle; (iii) directing at least a portion of the scattered or emitted electromagnetic radiation from the reference particle onto an array of detector elements of an active area of a two-dimensional detector, (iv) detecting at least a portion of the scattered or emitted electromagnetic radiation from the reference particle directed onto the plurality of detector elements, wherein at least a portion of the detector elements of the array generate output signals corresponding to intensities of the scattered or emitted electromagnetic radiation; and (v) measuring output signals for at least a portion of the detector elements of the array, thereby generating a reference particle detection signature of the intensities of the electromagnetic radiation scattered by the reference particle, the reference particle detection signature comprising a reference pattern of output signals of detector elements. In an embodiment, the steps of identifying and/or analyzing a particle detection signature comprise comparing the pattern of the output signals of the particle detection signature with the reference particle detection signature.

In another embodiment, the invention provides a method for detecting a particle in a fluid flow comprising the steps: (i) providing the fluid flow having the particle; (ii) exposing the fluid flow to a beam of electromagnetic radiation, wherein interaction between the particle and the beam generates scattered or emitted electromagnetic radiation; (iii) directing at least a portion of the scattered or emitted electromagnetic radiation onto a plurality of detector elements provided in an array of a two-dimensional detector, (iv) detecting at least a portion of the scattered or emitted electromagnetic radiation, wherein at least a portion of the detector elements of the array generate output signals corresponding to intensities of the scattered or emitted electromagnetic radiation; (v) determining a subset of the detector elements of the array, the subset comprising a plurality of detector elements, wherein each detector element of the subset has an output signal greater than or equal to a threshold value for a given detector element; (vi) transmitting to a processor only the output signals of the subset; and (vii) analyzing the output signals transmitted to the processor, thereby detecting the particle. In some methods of this aspect the detector elements are pre-filtered such that only output signals that exceed the threshold values for the detector elements, and optionally output signals from neighboring and/or directly neighboring detector elements are transmitted and processed. In some methods of the invention, the determining step comprises analyzing the output signals of the detector elements of the two-dimensional detector; and identifying detector elements having an output signal greater than the threshold value for a given detector element. As used herein, the term "subset" refers to a portion, but not all, of the detector elements of the two dimensional detector, such as a CMOS detector, and in some embodiments refers to detector elements that detect electromagnetic radiation scattered or emitted from the particle. In some methods, the subset comprises at least 3 neighboring or directly neighboring detector elements of the array, and optionally the subset comprises at least 10 neighboring or directly neighboring detector elements of the array. In some methods, the subset comprises 2 to 7 neighboring or directly neighboring detector elements of the array, and optionally the subset comprises 2 to 20 neighboring or directly neighboring detector elements of the array. In an embodiment, the subset further comprises from 0 to 50 or optionally 1 to 50, detector elements neighboring or directly neighboring each of the detector elements having an output signal greater than or equal to a threshold value for a given detector element.

In an embodiment of this aspect, the output signals of detector elements of the array are processed signals, for example, wherein each of the output signals has a background value subtracted for a given detector element in the array. In some embodiments of this aspect, each of the subtracted background values correspond to an average output signal for a given detector element in the array for detection conditions wherein no particle of interest is provided to the beam. In an embodiment, the minimum threshold values vary for different detector elements in the array. In an embodiment for example, the threshold value for a given detector element in the array is equal to or greater than 2.5 times the standard deviation of the noise of the given detector element of the array, and optionally the threshold value for a given detector element in the array is equal to 2.5 to 7 times the standard deviation of the noise of the given detector element of the array. In an embodiment, the method of this aspect further comprises the step of imaging at least a portion of the scattered or emitted electromagnetic radiation onto the detector elements of the array.

In another embodiment, the present invention provides a method for detecting a particle in a fluid flow comprising the steps of: (i) providing the fluid flow having the particle; (ii) exposing the fluid flow to a beam of electromagnetic radiation, wherein interaction between the particle and the beam generates scattered or emitted electromagnetic radiation; (iii) directing at least a portion of the scattered or emitted electromagnetic radiation onto a plurality of detector elements provided in an array of a two-dimensional detector, (iv) detecting at least a portion of the scattered or emitted electromagnetic radiation; (v) generating a plurality of detection frames, wherein each detection frame comprises a plurality of the output signals of the detector elements for a given time interval, (vi) combining a plurality of detection frames having output signals corresponding to detected intensities of the scattered or emitted electromagnetic radiation to generate a composite image of a particle detection event; (vii) analyzing the composite image, thereby detecting the particle. As used herein a composite image refers to a composite of data points resulting from combination of at least a portion of the output signals for a plurality of detection frames, optionally detection frames corresponding to a single particle detection event. In some embodiments, for example, scattering or emission from particles is captured over multiple detection frames, and at least a portion of the output signals from each frame are combined to produce a composite image of scattering from the particle. In some embodiments, the composite image is analyzed to determine the size or other physical dimension of the particle. As used herein, "detection frame" refers to a plurality of output signals for at least a portion of the two-dimensional detector, and optionally from a sub-array of the two-dimensional detector or subset of the detector elements of the two-dimensional detector. In this way, detection frames correspond to a plurality of individual measurements of electromagnetic radiation scattered, emitted or transmitted by the fluid containing particles.

A method of this embodiment further comprises identifying detection frames having output signals corresponding to detected intensities of electromagnetic radiation scattered or emitted by the particle. In some embodiments, the detection frames are generated at a rate of 0.5 kHz to 20 kHz, and optionally for some applications at a rate of 0.1 kHz to 2 kHz. In some methods, each of the detection frames corresponds to a time interval of 50 µs to 2 ms. In an embodiment, 1 to 100 detection frames are combined to generate the composite image, and optionally for some applications 1 to 20 detection frames are combined to generate the composite image. Some methods of this embodiment further comprise subtracting a reference frame from each of the detection frames. As used herein, the term reference frame refers to a plurality of background output signals for the detector elements in the array (or subset or sub-array thereof), wherein each background output signal is the average output signal for a given detector element in the array for detection conditions wherein no particle of interest is provided to the beam. In this way, reference frames correspond to a plurality of individual measurements of electromagnetic radiation scattered, emitted or transmitted by the fluid and/or the optical particle counter system in the absence of a particle of interest. In an embodiment, the reference frame is an average of 50 to 200 individual frames corresponding to detection conditions in the absence of a particle of interest and, thus, represents steady state values for each detector element of the array or subset or sub-array thereof. Subtraction of a reference frame from a detection frame enables detection and sizing of small particles that under some conditions generate scattered or emitted light signals less than the steady state values of the detector elements. Optionally, the reference frame is continuously updated in some methods. A method of this embodiment further comprises imaging at least a portion of the scattered or emitted electromagnetic radiation onto the detector elements of the array.

In another embodiment, the invention provides a method for detecting a particle in a fluid flow comprising the steps: (i) providing the fluid flow having the particle; (ii) exposing the fluid flow to a beam of electromagnetic radiation, wherein interaction between the particle and the beam generates scattered or emitted electromagnetic radiation; (iii) directing at least a portion of the scattered or emitted electromagnetic radiation onto a plurality of detector elements provided in an array of a two-dimensional detector, (iv) detecting at least a portion of the scattered or emitted electromagnetic radiation using a sub-array of the two-dimensional detector, wherein at least a portion of the detector elements of the sub-array generate output signals corresponding to intensities of the scattered or emitted electromagnetic radiation; (v) transmitting to a processor only the output signals of the detector elements corresponding to the sub-array or a portion thereof; and (vi) analyzing the output signals transmitted to the processor, thereby detecting the particle. As used herein, the term "sub-array" refers to a portion of an array of a two dimensional detector. Methods of the present invention utilizing output signals from a sub-array enable the ability to very rapidly read out a reduced area of the active area of the two-dimensional detector, thereby realizing high frequency and high sensitivity measurements for counting and sizing particles. In an embodiment, for example, the sub-array comprises 0.2% to 25% of the detector elements of the two-dimensional detector and, optionally the sub-array comprises 0.2% to 10% of the detector elements of the two-dimensional detector. In an embodiment, for example, the sub-array comprises 32×176 detection elements, and optionally for some applications 64×576 detection elements. In an embodiment, the two-dimensional detector has 400000 to 1300000 detection elements, and optionally is a CMOS detector. A method of this embodiment further comprises imaging at least a portion of the scattered or emitted electromagnetic radiation onto the detector elements of the array.

In an embodiment, the invention provides a method for detecting a particle in a fluid flow comprising the steps: (i) providing the fluid flow having the particle; (ii) exposing the fluid flow to a beam of electromagnetic radiation, wherein interaction between the particle and the beam generates scattered or emitted electromagnetic radiation; (ii) directing at least a portion of the scattered or emitted electromagnetic radiation onto a plurality of detector elements provided in an array of a two-dimensional detector; (iii) detecting at least a portion of the scattered or emitted electromagnetic radiation using a sub-array of the two-dimensional detector, wherein at least a portion of the detector elements of the sub-array generate output signals corresponding to intensities of the scattered or emitted electromagnetic radiation; (iv) determining a subset of the detector elements of the sub-array, the subset comprising a plurality of detector elements, wherein each detector element of the subset has an output signal greater than or equal to a threshold value for a given detector element; (v) transmitting to a processor only the output signals of the subset; and (vi) analyzing the output signals transmitted to the processor, thereby detecting the particle. In an embodiment, the determining step comprises analyzing the output signals of the sub-array; and identifying detector elements of the sub-array having an output signal greater than the threshold value for a given detector element. In an embodiment, the subset further comprises from 0 to 50 detector elements neighboring or directly neighboring each of the detector elements having an output signal greater than or equal to a threshold value for a given detector element. A method of this embodiment further comprises imaging at least a portion of the scattered or emitted electromagnetic radiation onto the detector elements of the array.

The present invention also provides optical imaging based particle sensing systems, including optical particle counters and analyzers, capable of identifying and analyzing particle detection signatures resulting from optical scattering or emission from particles. An optical particle analyzer of this aspect comprises: (i) an optical source for generating a beam of electromagnetic radiation; (ii) a chamber for flowing a fluid containing particles through the beam of electromagnetic radiation, thereby generating scattered or emitted electromagnetic radiation, wherein the fluid flow is characterized by a flow direction; (iii) an optical collection system for collecting and directing at least a portion of the scattered or emitted electromagnetic radiation onto a plurality of detector elements of an array of a two-dimensional detector, wherein at least a portion of the detector elements of the array generate output signals corresponding to intensities of the scattered or emitted electromagnetic radiation; and (iv) a processor operationally connected to the two-dimensional detector capable of identifying a particle detection signature comprising a pattern of a plurality of output signals of detector elements each having an output signal greater than or equal to a threshold value for a given detector element. In an embodiment, the processor is also capable of analyzing the shape of the particle detection signature and/or intensities of the output signals of the particle detection signature, so as to provide an indication of a characteristic of the particle(s), such as the size, shape and/or physical dimensions of the particles. In some systems of this aspect of the present invention, the optical collection system for collecting and directing at least a portion of the scattered or emitted electromagnetic radiation includes collection optics, such as a lens system, for imaging at least a portion of the scattered or emitted electromagnetic radiation onto the active area of the two-dimensional detector.

In a method of the invention, the fluid flow is a flow of liquid containing the particles. In a method of the invention, the fluid flow is a flow of gas containing the particles. In embodiments of the present invention, a combination of specific system components and specifications are selected so as to generate a particle detection signature from a particle scattering event having reproducible and readily identifiable features, such as a well defined geometric shape and/or intensity distribution. In a specific embodiment, for example, the length of a trajectory of the particle through the beam is selected over the range of 0.01 millimeters to 0.150 millimeters. In a specific embodiment, for example, the two-dimensional detector has a pixel dimension (detector element size) from 3 μm on a side to 50 μm on a side. In a specific embodiment, for example, the array of the two-dimensional detector has an active area selected over the range of 0.1 millimeters$^2$ to 5 centimeters$^2$. In a specific embodiment, for example, the fluid flow is provided with a flow velocity selected over the range of 1 centimeter $5^{-1}$ to 200 centimeters $s^{-1}$. In a specific embodiment, for example, the intensity profile of the signal reflects the intensity profile of the laser beam.

Analyzers of the present invention include volumetric optical particle counters and analyzers for detecting and/or characterizing particles in the entire volume of a sample. The invention also includes, however, non-volumetric optical particle counters and analyzers for detecting and/or characterizing particles in a portion of the volume of a sample.

In another aspect, the present invention provides a method for suppressing false detection events in an optical particle analyzer comprising the steps: (i) providing a fluid flow having particles to the optical particle counter; (ii) exposing the fluid flow to a beam of electromagnetic radiation, wherein interaction between the fluid flow having particles and the beam generates scattered or emitted electromagnetic radiation; (iii) directing at least a portion of the scattered or emitted electromagnetic radiation onto a plurality of detector elements provided in an array of a two-dimensional detector of the optical particle analyzer, (iv) detecting at least a portion of the scattered or emitted electromagnetic radiation from the particle directed onto the plurality of detector elements, wherein at least a portion of the detector elements of the array generate output signals corresponding to intensities of the scattered or emitted electromagnetic radiation; (v) measuring output signals for at least a portion of the detector elements of the array; and (vi) sensing a particle detection event upon identification of a particle detection signature comprising a pattern of a plurality of output signals of detector elements each having an output signal greater than or equal to a threshold value for a given detector element, thereby suppressing false detection events in the optical particle analyzer. In a specific embodiment of this aspect, the particle detection signature comprises a pattern of output signals of detector elements having an elongated shape, and in some embodiments comprises above-threshold output signals from at least 3 longitudinally adjacent, directly neighboring detector elements. In a specific embodiment of this aspect, the particle detection signature comprises a pattern of output signals of at least 2 neighboring detector elements having an output signal greater than or equal to a threshold value for a given detector element, and in some embodiments, a pattern of output signals of at least 2 directly neighboring detector elements having an output signal greater than or equal to a threshold value for a given detector element. In some embodiments of this aspect, the pattern of output signals includes output signals from at least 2 neighboring detector elements, optionally directly neighboring detector elements, provided along a longitudinal dimension of the particle detection signature.

In another aspect, the present invention provides a method of distinguishing a particle scattering event from other electromagnetic radiation generation or detection processes in an optical particle analyzer, comprising the steps of: (i) providing a fluid flow having particles to the optical particle counter; (ii) exposing the fluid flow to a beam of electromagnetic radiation, wherein interaction between the fluid flow having particles and the beam generates scattered or emitted electromagnetic radiation; (iii) directing at least a portion of the scattered or emitted electromagnetic radiation onto a plurality of detector elements provided in an array of a two-dimensional detector of the optical particle analyzer, (iv) detecting at least a portion of the scattered or emitted electromagnetic radiation from the particle directed onto the plurality of detector elements, wherein at least a portion of the detector elements of the array generate output signals corresponding to intensities of the scattered or emitted electromagnetic radiation; (v) measuring output signals for at least a portion of the detector elements of the array; and (vi) sensing a particle detection event upon identification of a particle detection signature comprising a pattern of a plurality of output signals of detector elements each having an output signal greater than or equal to a threshold value for a given detector element, wherein said particle detection signature comprises output signals from at least 3 directly neighboring detector elements positioned along a longitudinal axis, thereby distinguishing the particle scattering event from other electromagnetic radiation generation or detection processes in the optical particle analyzer. In a specific embodiment of this aspect, the particle detection signature comprises a pattern of output signals of detector elements having an elongated shape, and in some embodiments comprises above-threshold output signals from at least 3 longitudinally adjacent, directly neighboring detector elements. In a specific embodiment of this aspect, the particle detection signature comprises a pattern of output signals of at least 2 neighboring detector elements having an output signal greater than or equal to a threshold value for a given detector element, and in some embodiments, a pattern of output signals of at least 2 directly neighboring detector elements having an output signal greater than or equal to a threshold value for a given detector element. In some embodiments of this aspect, the pattern of output signals includes output signals from at least 2 neighboring detector elements, optionally directly neighboring detector elements, provided along a longitudinal dimension of the particle detection signature.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

BRIEF DESCRIPTION OF THE DRAWINGS

FIG. 2A provides a schematic of an optical geometry wherein the major axis of the cross sectional profile of shaped beam of electromagnetic radiation 110 is oriented parallel to the flow direction of the fluid (schematically shown by arrows), and FIG. 2B provides a schematic of an optical geometry wherein the major axis of the cross sectional profile of shaped beam of electromagnetic radiation 110 is oriented orthogonal to the flow direction of the fluid (schematically shown by arrows).

FIG. 4A shows a block drawing illustrating a two-dimensional image of scattered electromagnetic radiation from particles provided to a system of the present invention. The grid elements shown in FIG. 4A are detector elements corresponding to individual pixel elements of a CCD detector.

FIG. 7A provides a top view and FIG. 7B provides a side view.

DETAILED DESCRIPTION OF THE INVENTION

Figure 1A:
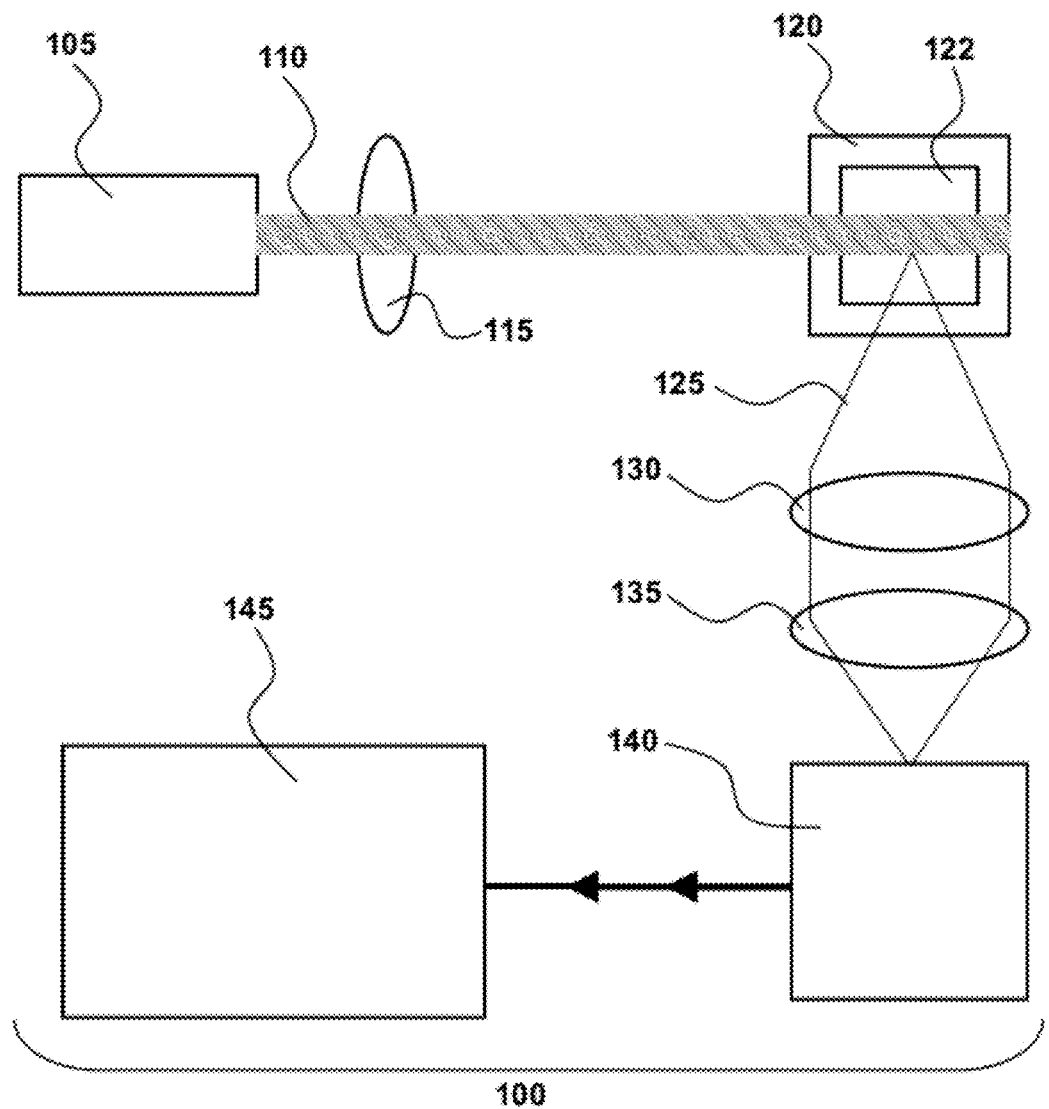
FIG. 1A provides a schematic diagram of a two dimensional imaging-based particle counter of the present invention useful for detecting and/or characterizing particles in liquid samples.

In general the terms and phrases used herein have their art-recognized meaning, which can be found by reference to standard texts, journal references and contexts known to those skilled in the art. The following definitions are provided to clarify their specific use in the context of the invention.

The expression "particle detection signature" and "detection signature" refer to a pattern comprising a plurality of output signals of detector elements each having an output signal greater than or equal to a threshold value for a given detector element of a detector array of a two dimensional optical detector. Particle detection signatures of the present invention are generated by two-dimensional detection of electromagnetic radiation scattered or emitted by particles. Particle detection signatures have a geometric shape and/or intensity distribution components useful for accurate detecting and characterizing of particles. Particle detection signatures of the present invention may be characterized in terms of a longitudinal component and/or a lateral component.

"Flow direction" refers to an axis parallel to the direction the bulk of a fluid is moving when a fluid is flowing. For fluid flowing through a straight flow cell, the flow direction is parallel to the path the bulk of the fluid takes. For fluid flowing through a curved flow cell, the flow direction may be considered tangential to the path the bulk of the fluid takes.

"Beam propagation axis" refers to an axis parallel to the direction of travel of a beam of electromagnetic radiation.

"Cross sectional profile" refers to a profile formed by a plane cutting through an object at a right angle to an axis of propagation or travel. For example the cross sectional profile of a beam of electromagnetic radiation is a profile of the beam formed by a plane perpendicular to the beam propagation axis. The cross sectional profile of a flow cell is a profile of the flow cell formed by a plane perpendicular to the flow direction.

"Major axis" refers to an axis parallel to the longest axis of a shape. For example, the major axis of an ellipse is parallel to the longest diameter of the ellipse, and the major axis of a rectangle is parallel to the long dimension of a rectangle.

"Minor axis" refers to an axis parallel to the shortest axis of a shape. For example, the minor axis of an ellipse is parallel to the shortest diameter of the ellipse, and the minor axis of a rectangle is parallel to the short dimension of a rectangle.

"Optical communication" refers to components which are arranged in a manner that allows light to transfer between the components.

"Optical axis" refers to a direction along which electromagnetic radiation propagates through a system.

"Two-dimensional detector" refers to an optical detector capable of spatially resolving input signals (e.g., electromagnetic radiation) in two dimensions across an active area of the detector. A two-dimensional detector is capable of generating an image, for example an image corresponding to an intensity pattern on the active area of the detector. A preferred two-dimensional detector comprises an array of individual detector elements, also referred herein as pixels; for example: a two-dimensional array of photodetectors, a charge-coupled device (CCD) detector, a complementary metal-oxide-semiconductor (CMOS) detector, a metal-oxide-semiconductor (MOS) detector, an active pixel sensor, a microchannel plate detector, a two-dimensional array of photomultiplier tubes, a two-dimensional array of photodiodes, a two-dimensional array of phototransistors, a two-dimensional array of photoresistors, or a photoconductive film.

"Optical source" refers to a device or device component that is capable of delivering electromagnetic radiation to a sample. The term is not limited to visible radiation, such as by a visible light beam, but is used in a broad sense to include any electromagnetic radiation. The optical source may be embodied as a laser or laser array, such as a diode laser, diode laser array, diode laser pumped solid state laser, LED, LED array, gas phase laser, solid state laser, to name a few examples.

The term "electromagnetic radiation" and "light" are used synonymously in the present description and refer to waves of electric and magnetic fields. Electromagnetic radiation useful for the methods of the present invention include, but is not limited to ultraviolet light, visible light, infrared light, or any combination of these having wavelengths between about 100 nanometers to about 15 microns.

The expression "detecting a particle" broadly refers to sensing, identifying the presence of and/or characterizing a particle. In some embodiments, detecting a particle refers to counting particles. In some embodiments, detecting a particle refers to characterizing and/or measuring a physical characteristic of a particle, such as diameter, cross sectional dimension, shape, size, aerodynamic size, or any combination of these.

"Particles" refers to small objects which are often regarded as contaminants. A particle can be any material created by the act of friction, for example when two surfaces come into mechanical contact and there is mechanical movement. Particles can be composed of aggregates of material, such as dust, dirt, smoke, ash, water, soot, metal, minerals, or any combination of these or other materials or contaminants. "Particles" may also refer to biological particles, for example, viruses, spores and microorganisms including bacteria, fungi, archaea, protists, other single cell microorganisms and specifically those microorganisms having a size on the order of 1-15 μm. A particle may refer to any small object which absorbs or scatters light and is thus detectable by an optical particle counter. As used herein, "particle" is intended to be exclusive of the individual atoms or molecules of a carrier fluid, for example water molecules, oxygen molecules, helium atoms, nitrogen molecules, etc. Some embodiments of the present invention are capable of detecting, sizing, and/or counting particles comprising aggregates of material having a size greater than 10 nm, 20 nm, 30 nm, 50 nm, 100 nm, 500 nm, 1 µm or greater, or 10 µm or greater. Specific particles include particles having a size selected from 20, nm, 30 nm to 50 nm, 50 nm to 50 µm, a size selected from 100 nm to 10 µm, or a size selected from 500 nm to 5 µm.

The terms "aerosol optical particle counter", "optical particle counter" and "particle counter" are used interchangeably herein and refer to systems capable of detecting particles suspended in a fluid, systems capable of determining the sizes of particles suspended in a fluid, systems capable of counting particles suspended in a fluid, systems capable of classification of particles suspended in a fluid, or any combination of these. A typical liquid or aerosol optical particle counter is comprised of several components, such as a source for generating a beam of electromagnetic radiation, optics for directing the beam into a region where a fluid sample is flowing, for example a liquid or gas flowing through a flow cell. A typical optical particle counter is also comprised of a photodetector, such as a two-dimensional optical detector, and collection optics for detecting electromagnetic radiation which is scattered by or emitted by particles which pass through the beam, and other electronics for the processing and analysis of electrical signals produced by the photodetector including current to voltage converters and signal filtering and amplification electronics. An optical particle counter may also be comprised of a pump for creating a flow for introducing a fluid sample to the detection region where the electromagnetic beam is present.

The present invention provides two dimensional imaging-based methods and systems for detecting and characterizing particles in a fluid. Methods and systems of the present invention generate, identify and/or analyze particle detection signatures having geometric shapes and intensity distributions useful for accurately detecting and characterizing particles and for suppressing false counts.

FIG. 1A provides a schematic diagram of a two dimensional imaging-based particle counter 100 of the present invention useful for detecting and/or characterizing particles in liquid samples. As shown in FIG. 1A, optical source 105, such as a laser or light emitting diode optical source, generates beam of electromagnetic radiation 110 that is directed on beam shaping optics 115, such as one or more focusing lenses. Shaped beam of electromagnetic radiation 110 is directed onto flow cell 120 having flow chamber 122 for confining the fluid flow having particles provided therein. Interaction of beam of electromagnetic radiation 110 and particles in the fluid provided in flow chamber 122 of flow cell 120 generates scattered electromagnetic radiation. A portion of scattered electromagnetic radiation 125 is collected by collection optics 130 and 135, for example an aspheric lens system, and imaged onto a plurality of detector elements of an array of two-dimensional detector 140. In an embodiment, two-dimensional detector 140 is a CCD detector or camera, a CMOS detector, a MOS detector, an active pixel sensor, a microchannel plate detector, or a two-dimensional array of photodiodes. In a preferred embodiment, two-dimensional detector 140 is an image camera system. At least a portion of detector elements of the detector elements of the two dimensional array generate output signals corresponding to intensities of the scattered or emitted electromagnetic radiation. At least portion of the output signals from detector elements of two-dimensional detector 140 are measured and analyzed, optionally by processing electronics 145. Two-dimensional detector 140 and/or processing electronics 145 are configured to identify and analyze a particle detection signature comprising a pattern of a plurality of output signals of detector elements each having an output signal greater than or equal to a threshold value for a given detector element.

Figure 1B:
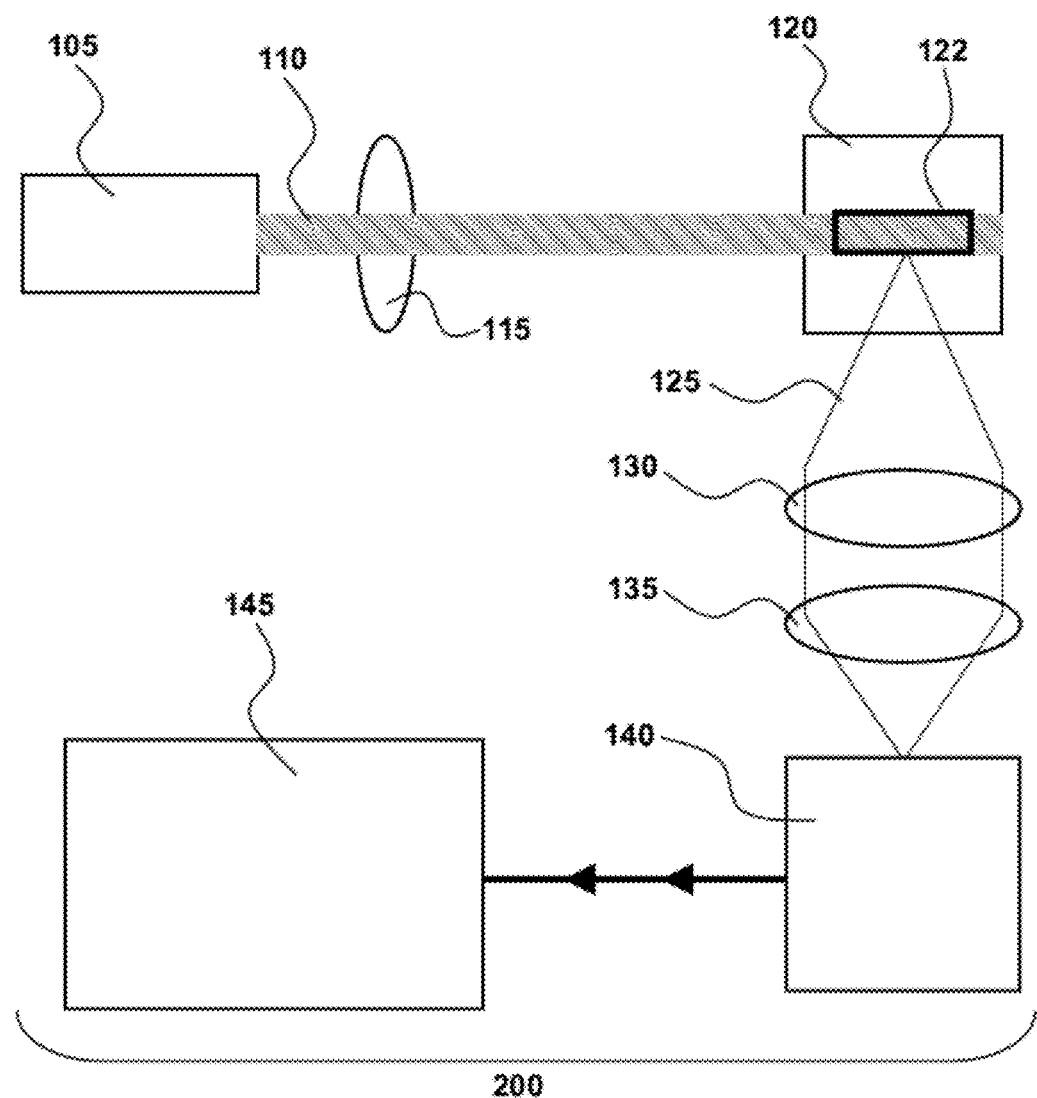
FIG. 1B provides a schematic diagram of a two dimensional imaging-based particle counter of the present invention providing volumetric analysis of particles in liquid samples.

For ease of illustration, FIG. 1A exemplifies an embodiment of the present invention having an optical geometry wherein only a portion of the cross sectional profile of flow chamber 122 is illuminated by beam of electromagnetic radiation 110. As will be understood by those having skill in the art, the present invention may integrate a wide range of optical geometries and beam dimensions for exposing a fluid to the beam of electromagnetic radiation. For example, the present invention includes optical geometries and beam dimensions wherein the entire cross sectional profile of flow chamber 122 is illuminated by beam of electromagnetic radiation 110, thereby providing volumetric analysis. FIG. 1B provides a schematic diagram of a two dimensional imaging-based particle counter 200 of the present invention providing volumetric analysis of particles in liquid samples. As shown in FIG. 1B, beam 110 entirely overlaps flow chamber 122, so as to enable a volumetric measurement.

Figure 2:
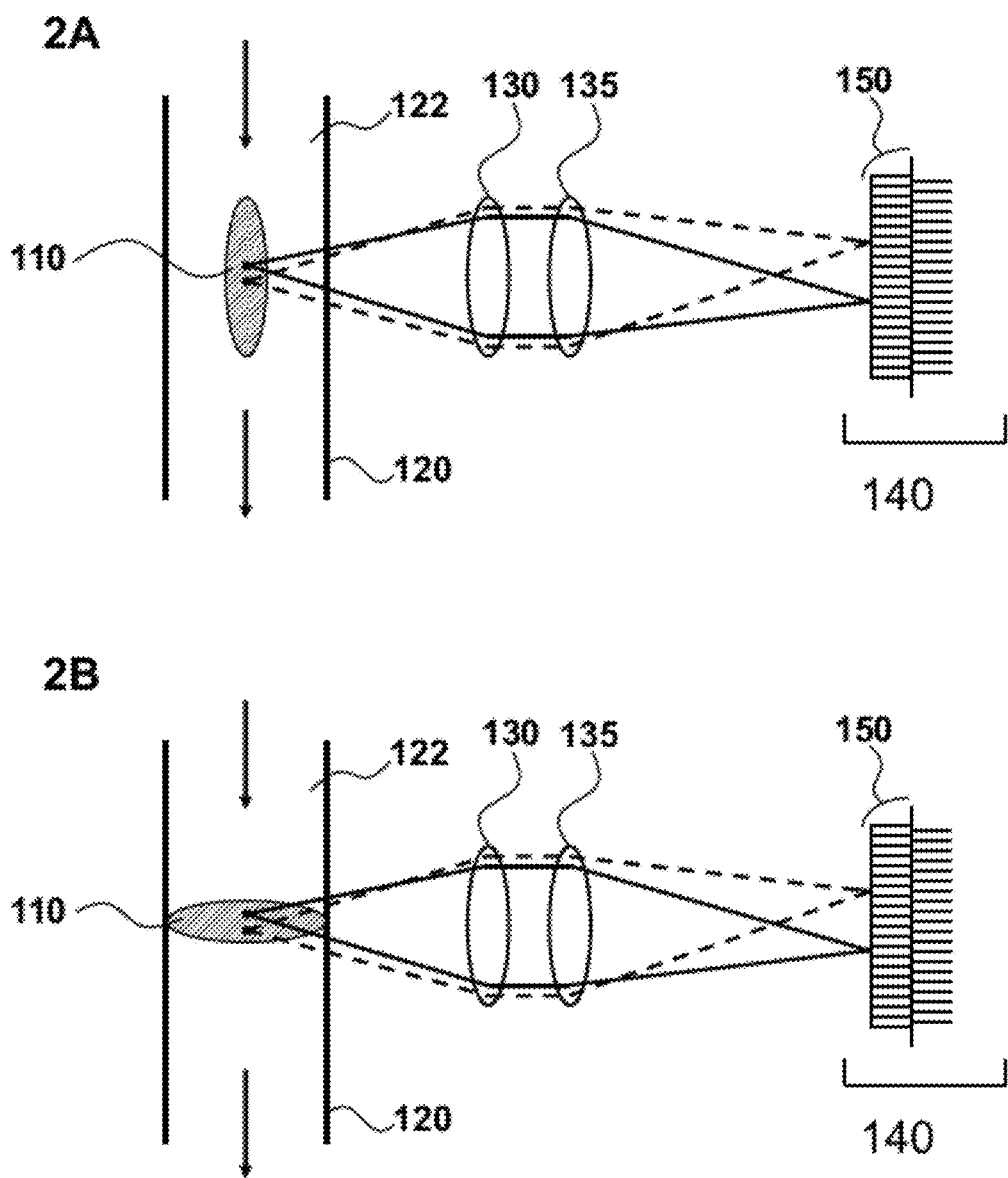
FIGS. 2A and 2B provide a top plan view of the imaging detection components of a two dimensional imaging-based particle counter 100.

FIGS. 2A and 2B provide a top plan view of the imaging-based detection components of two dimensional imaging-based particle counter 100. Drawing element 110 shows a cross section of shaped beam of electromagnetic radiation 110 propagating along a propagation axis (into and out of the plane of the paper) that intersects flow cell 120 and exposes fluid containing particles confined in flow chamber 122 to electromagnetic radiation. FIG. 2A provides a schematic of an optical geometry wherein the major axis of the cross sectional profile of shaped beam of electromagnetic radiation 110 is oriented parallel to the flow direction of the fluid (schematically shown by arrows), and FIG. 2B provides a schematic of an optical geometry wherein the major axis of the cross sectional profile of shaped beam of electromagnetic radiation 110 is oriented orthogonal to the flow direction of the fluid (schematically shown by arrows). FIGS. 2A and 2B also provide ray diagrams showing scattered electromagnetic radiation from particles (schematically shown as solid circles in FIGS. 2A and 2B) flowing through the flow chamber 122 of flow cell 120. As shown in these figures, scattered light is collected by collection optics 130 and 135 and imaged onto a plurality of individual detector elements of two-dimensional array 150 of a two-dimensional detector 140. As shown by the ray diagrams in FIGS. 2A and 2B, spatial information relating to the electromagnetic radiation scattered by the particle(s) is retained via the present two-dimensional imaging techniques. Signals from detector elements of two-dimensional array 150 are processed and analyzed in real time by two-dimensional detector 140 and or processing electronics 145 to indentify and or analyze particle detection signatures.

Figure 3:
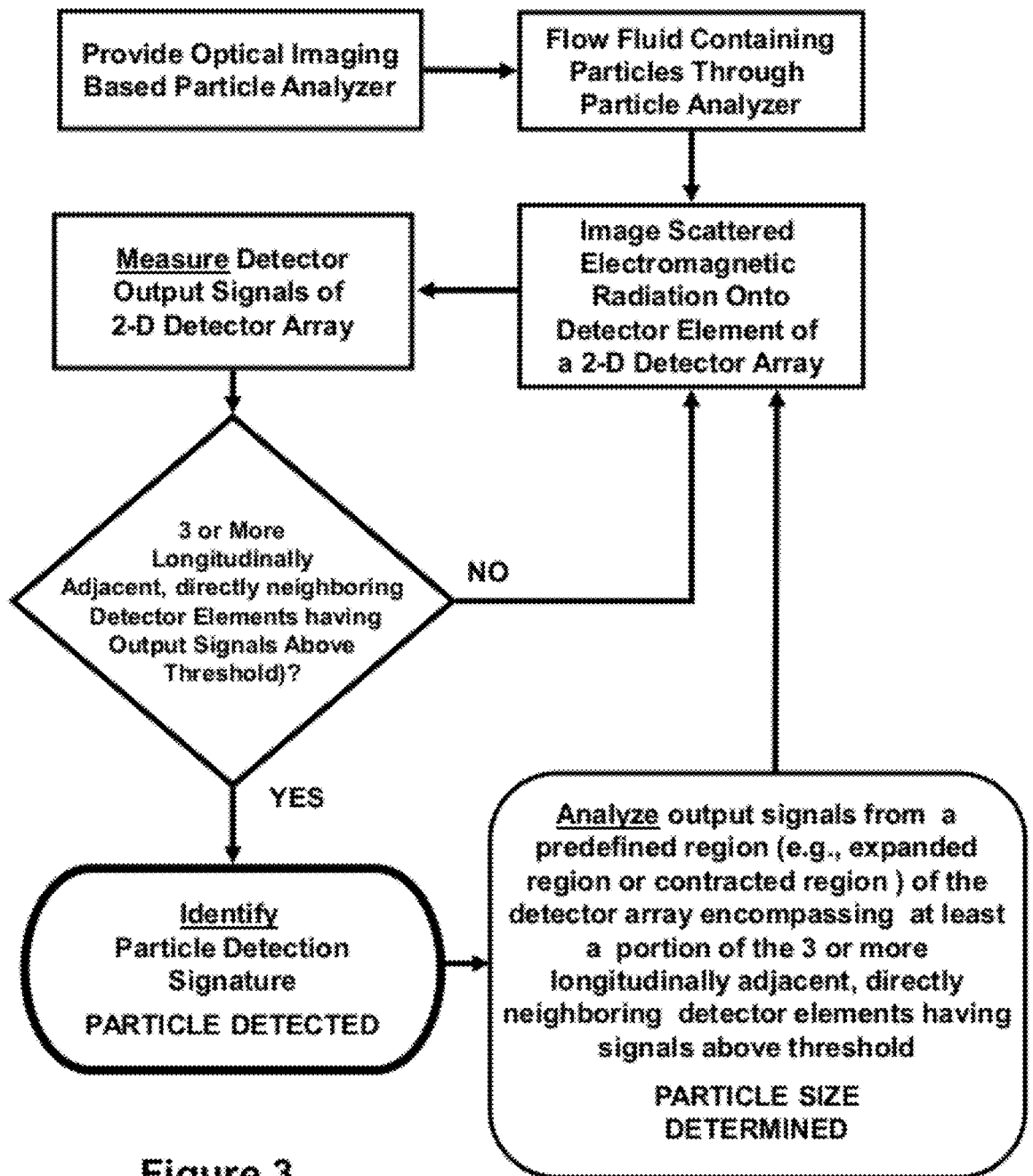
FIG. 3 provides a process flow diagram for a specific method of the present invention for detecting and optionally characterizing particles in a fluid using the two dimensional imaging-based particle counter of FIGS. 1 and 2.

FIG. 3 provides a process flow diagram for a specific method of the present invention for detecting and, optionally characterizing the size of, particles in a fluid using the two dimensional imaging-based particle analyzer of FIG. 1A or 1B. As shown in this figure, the imaging-based particle analyzer is provided and a fluid (gas or liquid) containing particles is flowed through the analyzer. Electromagnetic radiation scattered by particles in the fluid is imaged onto detector elements of a two-dimensional array of a two-dimensional detector. Output signals from the detector elements of the array are periodically measured and analyzed so as to identify a particle detection signature indicative of scattering from particles in the analyzer. In the specific embodiment shown in FIG. 3, output signals corresponding to detector elements of the array are analyzed so as to identify the occurrence of 3 or more longitudinally adjacent, directly neighboring detector elements having output signals larger than a threshold value preselected for each detector element in the array, which indicates a particle detection signature. Identification of the particle detection signature in this embodiment results in a determination that a particle is detected. In an embodiment, output signals corresponding to detector elements are analyzed so as to identify the occurrence of 3 or more longitudinally adjacent, directly neighboring detector elements having output signals 2.5 times larger than the standard deviation of the noise of a given detector element of the array, optionally 2.5-5 times larger than the standard deviation of the noise of a given detector element of the array, thereby indicating a particle detection signature and resulting in a determination that a particle has been detected. As described above, methods and systems of the present invention may optionally employ threshold values comprising a multiple (e.g., 2.5 or 2.5-5 times) the standard deviation of the output signals for the detector element for detection conditions in the absence of scattered or emitted electromagnetic radiation from a particle of interest (e.g., the background values for the detector element).

Optionally, the method shown in FIG. 3 further comprises the step of analyzing signals from a predefined region of the detector array, for example a region encompassing the 3 or more longitudinally adjacent, directly neighboring detector elements having signals above threshold or a portion of these detector elements. The predefined region of the array in some embodiments is an expanded region (i.e., including additional detector elements other than the 3 or more longitudinally adjacent, directly neighboring detector elements having signals above threshold). Alternatively, in some embodiments, the predefined region of the array in some embodiments is a contracted region (i.e., including less than all of the 3 or more longitudinally adjacent directly neighboring detector elements having signals above threshold). Analysis of the output signals of detector elements in the predefined region of the array in this embodiment may be carried out by a range of signal processing techniques including, but not limited to, integrating selected output signals of detector elements of the detector array, summing selected output signals of detector elements of the detector array, and averaging selected output signals of detector elements of the detector array. In some embodiments, the analysis step is carried out by comparing output signals or values derived from output signals to one or more predetermined values established upon calibration of the two-dimensional imaging-based particle analyzer. Analysis of the output signals of detector elements of the predefined region of the array results in a determination of the size of the particle.

FIG. 4A shows a block drawing illustrating a two-dimensional image of electromagnetic radiation scattered by particles in a two-dimensional imaging-based analyzer of the present invention. The particles imaged in these experiments are polystyrene latex spheres having a diameter of 125 nanometers. The grid elements shown in FIG. 4A are detector elements corresponding to individual pixel elements of a CCD detector. Six particle detection signatures 505, 510, 515, 520, 525 and 530 are clearly visible in the image. The different positions of the particle detection signatures correspond to different positions of particles in the flow chamber passing through the beam of electromagnetic radiation. In this embodiment of the present invention, the particle detection signatures 505, 510, 515, 520, 525 and 530 comprise a pattern of a plurality of output signals of at least 3 adjacent, directly neighboring detector elements having output signals larger than 3 times the standard deviation of the noise of a given detector element. Particle detection signature 530, for example, comprises a pattern of 15 output signals.

Also shown on FIG. 4A is longitudinal axis 570 and lateral axis 575. Each of particle detection signatures 505, 510, 515, 520, 525 and 530 may further be characterized by a longitudinal component comprising a series of directly neighboring detector elements extending a direction parallel to longitudinal axis 570. In an embodiment, for example, each of particle detection signatures 505, 510, 515, 520, 525 and 530 further are characterized by a longitudinal component comprising a the largest series of directly neighboring detector elements extending a direction parallel to longitudinal axis 570. As shown in FIG. 4A, particle detection signatures 505, 510, 515, 520, 525 and 530 are elongated and substantially rectangular in shape. Specifically, particle detection signatures 505, 510, 515, 520, 525 and 530 are characterized by a longer longitudinal component extending a direction parallel to longitudinal axis 570 and a shorter lateral component extending a direction parallel to lateral axis 575. The longer dimension of the rectangular shape (i.e., dimension extending the direction of longitudinal axis 570) corresponds to the flow direction of the particle(s) through the beam of electromagnetic radiation.

Figure 4B:
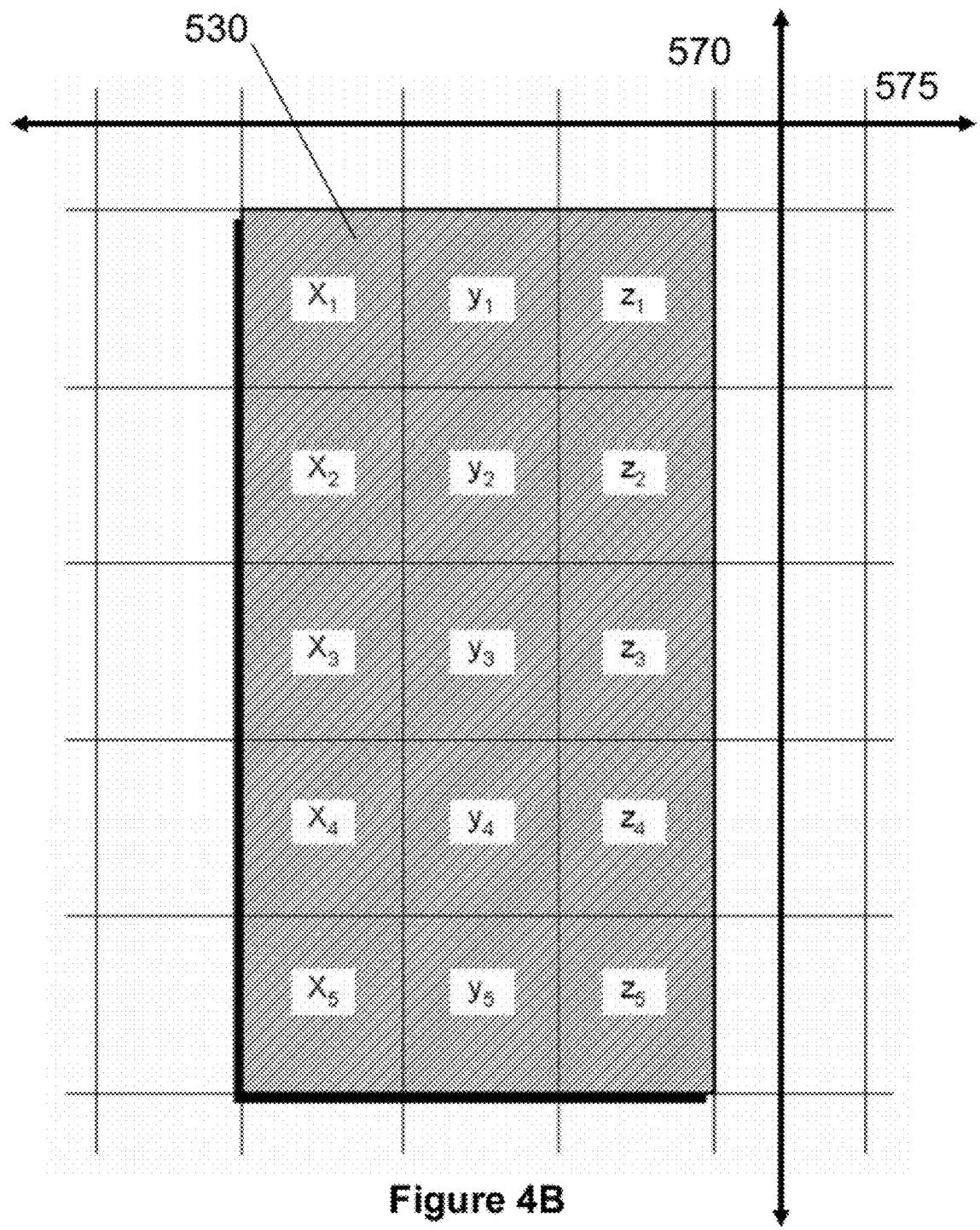
FIG. 4B shows an expanded view of particle detection signature 530 shown in FIG. 4A.

FIG. 4B shows an expanded view of particle detection signature 530 shown in FIG. 4A. The intensity values of the pattern of output signals are shown as $X_1$-$X_5$, $Y_1$-$Y_5$ and $Z_1$-$Z_5$. Each of $X_1$-$X_5$, $Y_1$-$Y_5$ and $Z_1$-$Z_5$ have values that exceed the threshold value for a given detector element, for example having values that are at least 3 times the standard deviation of the noise of for a given detector element. The output signals are longitudinally aligned for a given set of $X_1$-$X_5$, $Y_1$-$Y_5$ or $Z_1$-$Z_5$. In some embodiments, the distribution of intensity values for output signals $X_1$-$X_5$, $Y_1$-$Y_5$ and $Z_1$-$Z_5$ provide information regarding the size and/or shape of the particle(s) interacting with the beam of electromagnetic radiation. Also shown on FIG. 4A is longitudinal axis 570 and lateral axis 575. As shown in FIG. 4B, particle detection signature 530 has a longitudinal component comprising 5 directly neighboring detector elements. The longitudinal component of particle detection signature 530 may comprise any one of the series of detector elements: $X_1$-$X_5$, $Y_1$-$Y_5$ and $Z_1$-$Z_5$. As shown in FIG. 4B, particle detection signature 530 has a lateral component comprising 3 directly neighboring detector elements. The lateral component of particle detection signature 530 may comprise any one of the series of detector elements: $X_1Y_1Z_1$, $X_2Y_2Z_2$, $X_3Y_3Z_3$, $X_4Y_4Z_4$, and $X_5Y_5Z_5$.

Figure 5A:
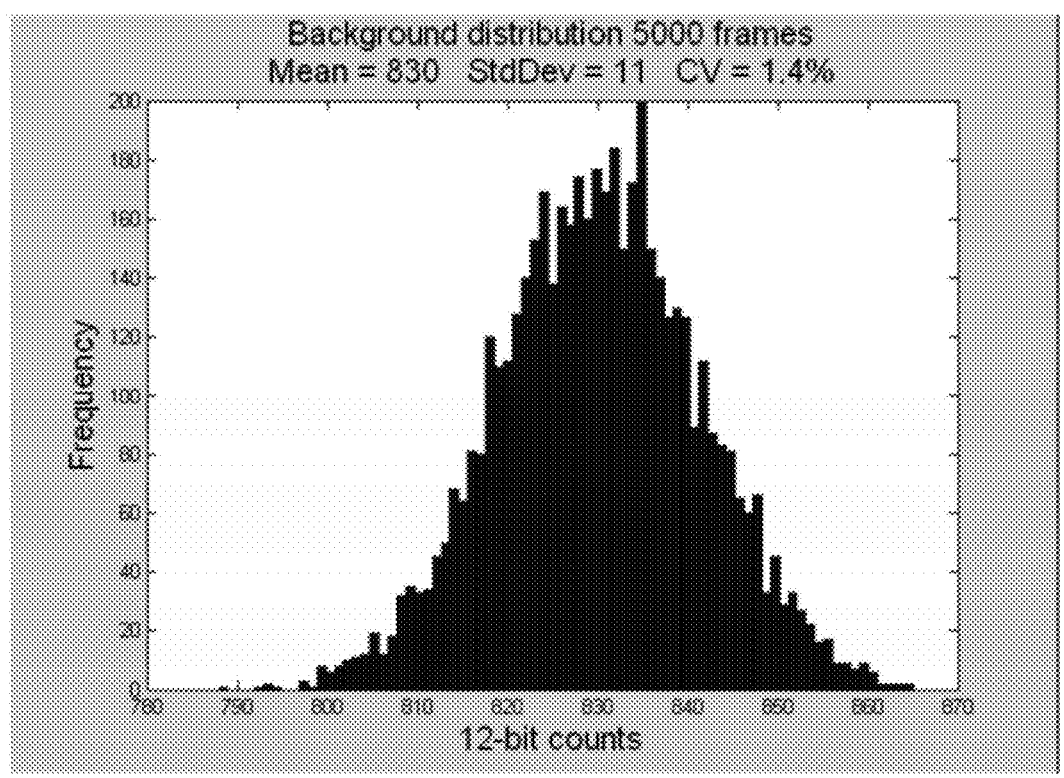
FIGS. 5A and 5B provide example experimental data showing a noise distribution for a detector element of a two-dimensional detector array relevant to establishing threshold values in the methods and systems of the present invention.
Figure 5B:
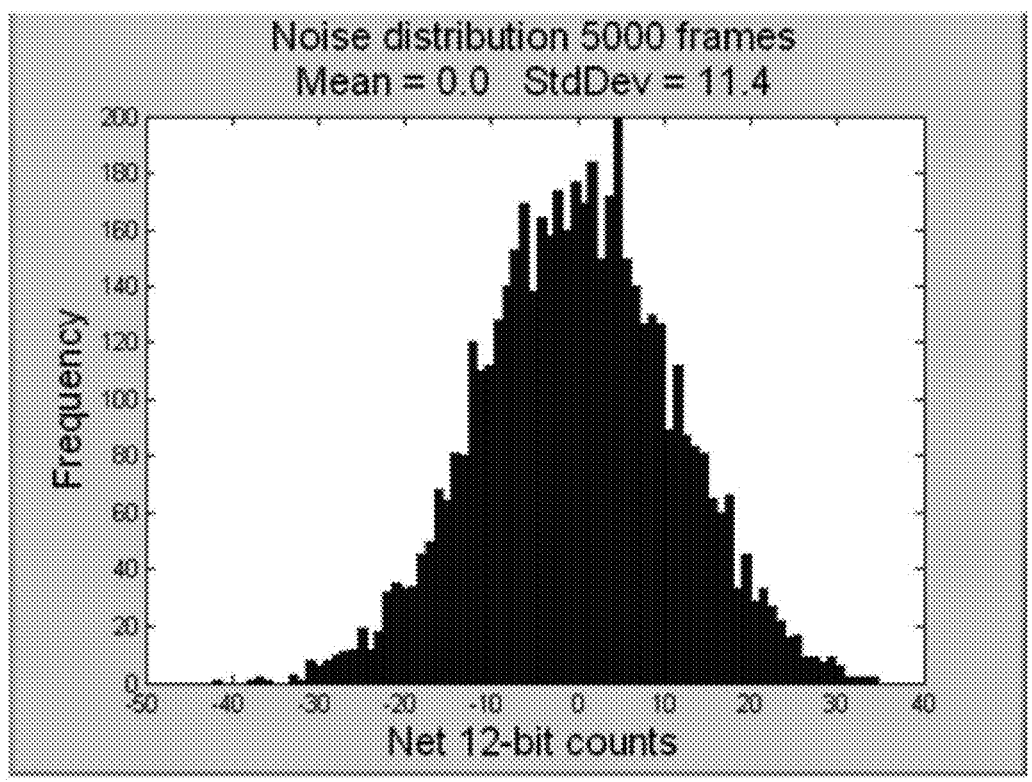

FIGS. 5A and 5B provide example experimental data showing a noise distribution for a detector element of a two-dimensional detector array relevant to establishing threshold values in the present invention. In these figures, frequency is plotted on the y-axis and 12-bit counts is plotted on the x-axis. The data is from a single pixel of a detector array exposed 5000 times (i.e., 5000 frames). FIG. 5A shows the background, which is both the steady-state light level plus the noise. FIG. 5B shows the same data with the steady-state level subtracted, leaving just the noise. The Standard deviation of the noise distribution is equal to 11.4. This value is useful in the present invention for establishing threshold values. In an embodiment, for example, the threshold value for a given detector element is set at approximately 3 times the standard deviation of the noise distribution for a given detector element, or a value of about 34.2 for this example.

Figure 6:
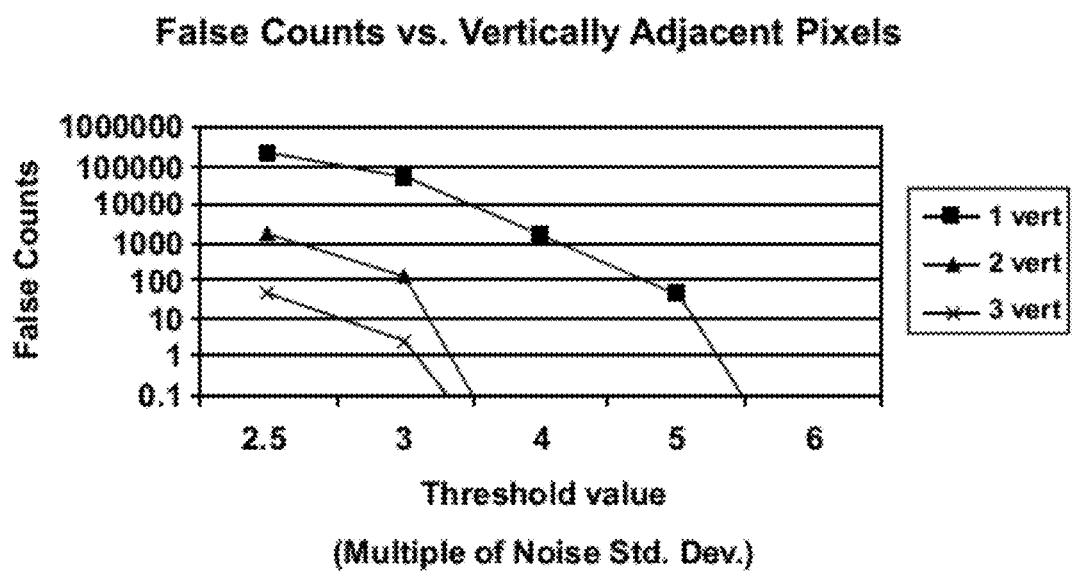
FIG. 6 shows a plot of false count rate verse threshold value (expressed in multiple of the noise of the standard deviation) for a range of image analysis conditions.

FIG. 6 shows a plot of false count rate verse threshold value (expressed in multiples the standard deviation of the noise distribution) for a range of image analysis conditions. The plot corresponding to (1 vert) corresponds to conventional particle detection analysis conditions wherein a particle detection is determined in the event that a single detector element equals or exceeds a preselected threshold value. The plot corresponding to (2 vert) corresponds to analysis conditions wherein particle detection is determined in the event that two longitudinally directly neighboring detector elements equal or exceed a preselected threshold value. This method, therefore, utilizes a particle detection signature comprising a pattern of output signals from two directly adjacent neighboring detector elements equal to or exceeding a given threshold value The plot corresponding to (3 vert) corresponds to analysis conditions wherein particle detection is determined in the event that three longitudinally directly neighboring detector elements equal or exceed a preselected threshold value. This method, therefore, utilizes a particle detection signature comprising a pattern of output signals from three directly adjacent neighboring detector elements equal to or exceeding a given threshold value As shown in this plot, image analysis based on identifying a two-dimensional detector signature having a plurality of longitudinally directly adjacent detector elements exceeding a threshold value (i.e., 2 vert and 3 vert plots) results in significantly less false counts. FIG. 6 also demonstrates that the use of particle detection signatures comprising output signals from a plurality of directly adjacent detector elements allows threshold values to be set significantly lower, thereby enabling detection and size characterization of smaller particles (e.g. diameters less than 0.1 micron).

The invention may be further understood by the following non-limiting examples.

EXAMPLE 1

Two Dimensional Imaging-Based Optical Particle Counter

The performance of an imaging-based optical particle counter of the present invention was experimentally evaluated. The optical particle counter of this Example uses a non-orthogonal optical geometry to allow high resolution, two-dimensional imaging of light scattered from particles in a fluid flow (e.g., liquid phase particle counting). The results provided herein demonstrate that the present imaging-based optical particle counter provides a robust sensing platform providing enhanced sensitivity over conventional optical particle counters.

One challenge for particle counting in ultra pure deionized (DI) water is that under many conditions such samples, for example as used in semiconductor fabrication or pharmaceutical production facilities, are very clean and typically include small numbers of very small particles. Deionized water is typically prepared by passing through one or more ion exchange resins to remove ion impurities and may be filtered one or more times before or after ion exchange to remove additional particulates and other impurities. A typical particle concentration for ultra pure deionized water is very small, for example, less than 0.1 parts per trillion (particles by volume at 200 counts per liter for particles greater than 50 nm). Further, in some commercially relevant conditions, non volatile residue (NVR), metallic and other ions exceed the concentration of particles by more than 4 orders of magnitude.

In traditional optical particle counters, molecular scattering from the carrier fluid (e.g., water) creates noise that can be a significant factor limiting the ability of the counter to detect and size characterize low numbers of small particles (e.g., less than 100 nanometers). For high purity conditions, for example, the level of radiation scattered from the carrier fluid detected by the optical detector of the particle counter is often larger than the intensity of scattered light from particles in the fluid. When the background signal is assumed to be a DC signal and is blocked, noise may result from variations in the background, thereby decreasing sensitivity and potentially contributing to the occurrence of false counts, which seriously undermines the reliability of the particle counter. The amount of noise on the detector is generally proportional to the square root of the DC noise level; for example, if the scattering levels increase by a factor of 4, the noise level will increase by a factor of 2.

To address this limitation, some optical particle counters reduce the total amount of molecular scattering detected by dividing the sample volume into smaller sections. The use of array detectors, for example, enables higher sensitivity particle counters by mapping the small sample volume sections onto the individual detector array elements. This technique, however, is currently limited to the use of one dimensional array detectors having 5 to 20 detector elements. The present invention implements two dimensional array detection using detectors having thousands or even millions of detector elements. The present invention also implements digital signal acquisition and processing methods.

To address the limitations of conventional systems, optical particle counters of the present invention divide the sample volume into thousands or millions of parts, digitizing the signal and utilizing advanced signal processing software and electronic systems to analyze particle detection events. By mapping the sample volume onto a two dimensional array (e.g., an array of 1 million pixels or more), the background radiation levels from even a high power laser remain low enough for sensitive detection of very small particles, for example particles about 100 nm or less, about 70 nm or less, than about 50 nm or less and/or about 40 nm or less in cross sectional dimension. This aspect of the present invention allows effective integration of very high power optical sources resulting in enhanced sensitivity. In addition, incorporation of high efficiency detectors in the present particle counters further increases the detection sensitivity by increasing signal to noise ratios.

One advantage of using a particle sensor comprising a two dimensional array detector, amongst others, is that the radiation signal scattered from a particle provides a unique pattern of pixel intensities, allowing for signals arising from particle scattering events to be efficiently discriminated from non particle signals including, for example, molecular scatter or high-energy photons (e.g., cosmic rays) striking the detector elements. Additionally, as the sample volume is mapped across the two dimensional detector, scattering from the walls of the optical cell (and/or contamination on the walls) can be effectively separated out so as not to affect the detection sensitivity of other areas of the sample volume where scattering from particles is occurring.

Another advantage of the particle sensors described herein is the ability to record particle detection events while operating, for example saving images detected by the two dimensional array detector. This can allow for off-line analysis of particle detection events, for example for further analysis and consideration. Further, the present optical particle counters provide for direct visualization of the flow cell using a two dimensional array detector. This configuration allows for real time optimization, troubleshooting, detection of impurities on or in the flow cell and/or detection of other problems.

Figure 7A:
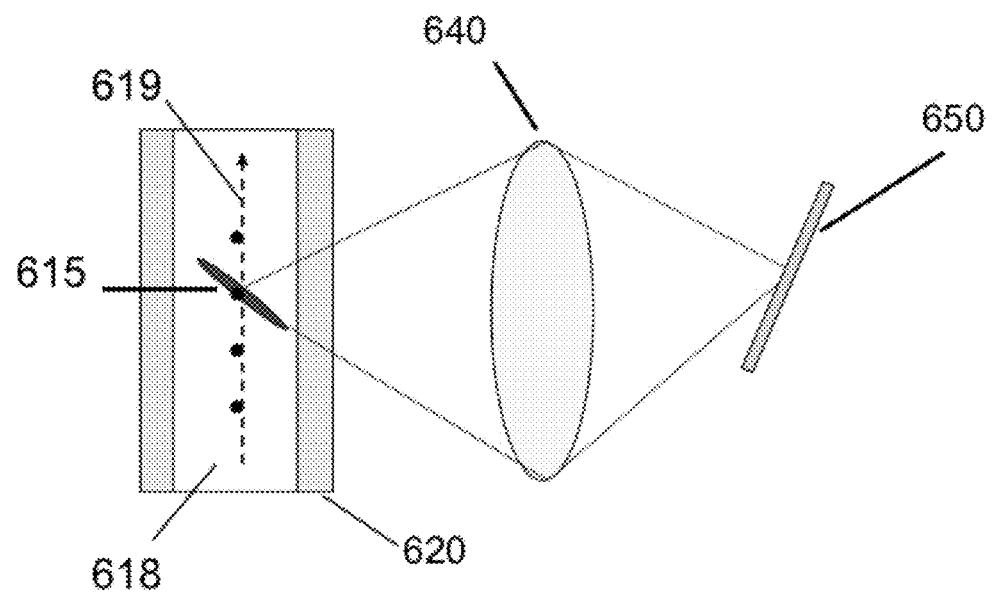
FIGS. 7A and 7B illustrates an optical geometry for imaging-based detection in the present invention utilizing a two dimensional array detector and non-orthogonal detection geometry.
Figure 7B:
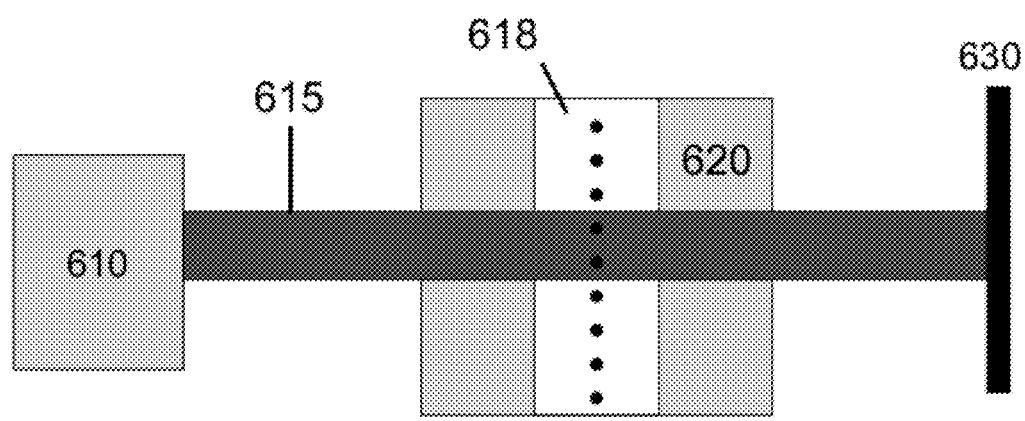

FIGS. 7A and &B illustrates an optical geometry for imaging-based detection in the present invention utilizing a two dimensional array detector and non-orthogonal detection geometry. FIG. 7A provides a top view and FIG. 7B provides a side view. A laser optical source 610 provides beam of electromagnetic radiation 615 having a narrow beam profile (e.g., the laser beam major axis is greater than the laser beam minor axis), which is directed through the flow cell 620 having a fluid 618 containing particles. The particles are schematically illustrated as solid circles in FIGS. 7A and 7B. As illustrated in these figures, fluid 618 is provided to flow cell 620 such that it flows in a preselected flow direction (shown schematically as dotted line 619). In the embodiment shown in FIGS. 7A and 7B, the beam passes from the flow cell to beam stop 630. As particles passing through the flow cell are illuminated by the laser beam 615, scattered radiation is generated, at least a portion of which is collected by an optical collection system comprising lens 640 and directed to a two dimensional detector array 650 provided in a tilted detector orientation. This detector orientation of two dimensional detector array 650 is governed by the angle of beam 615 provided to flow cell 615 with respect to the flow direction 619, so as to provide effective imaging of scattered electromagnetic radiation onto the active area of two dimensional detector array 650.

Figure 8:
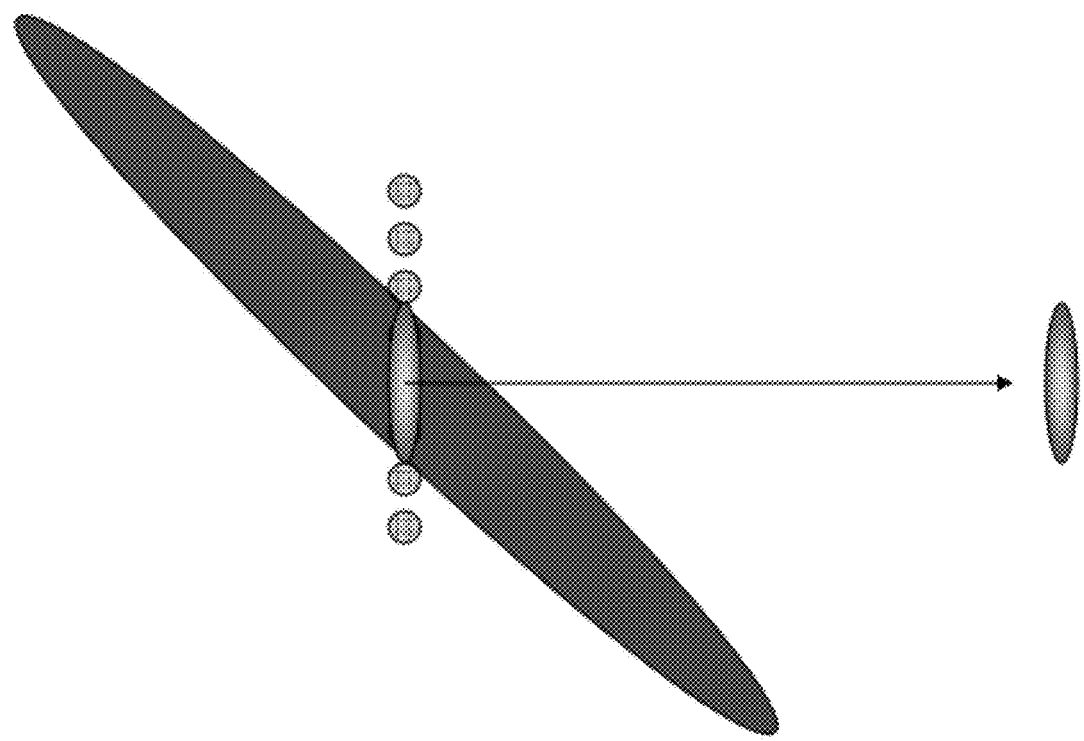
FIG. 8 shows a particle passing through the laser creating a scattered light streak on the detector.
Figure 9:
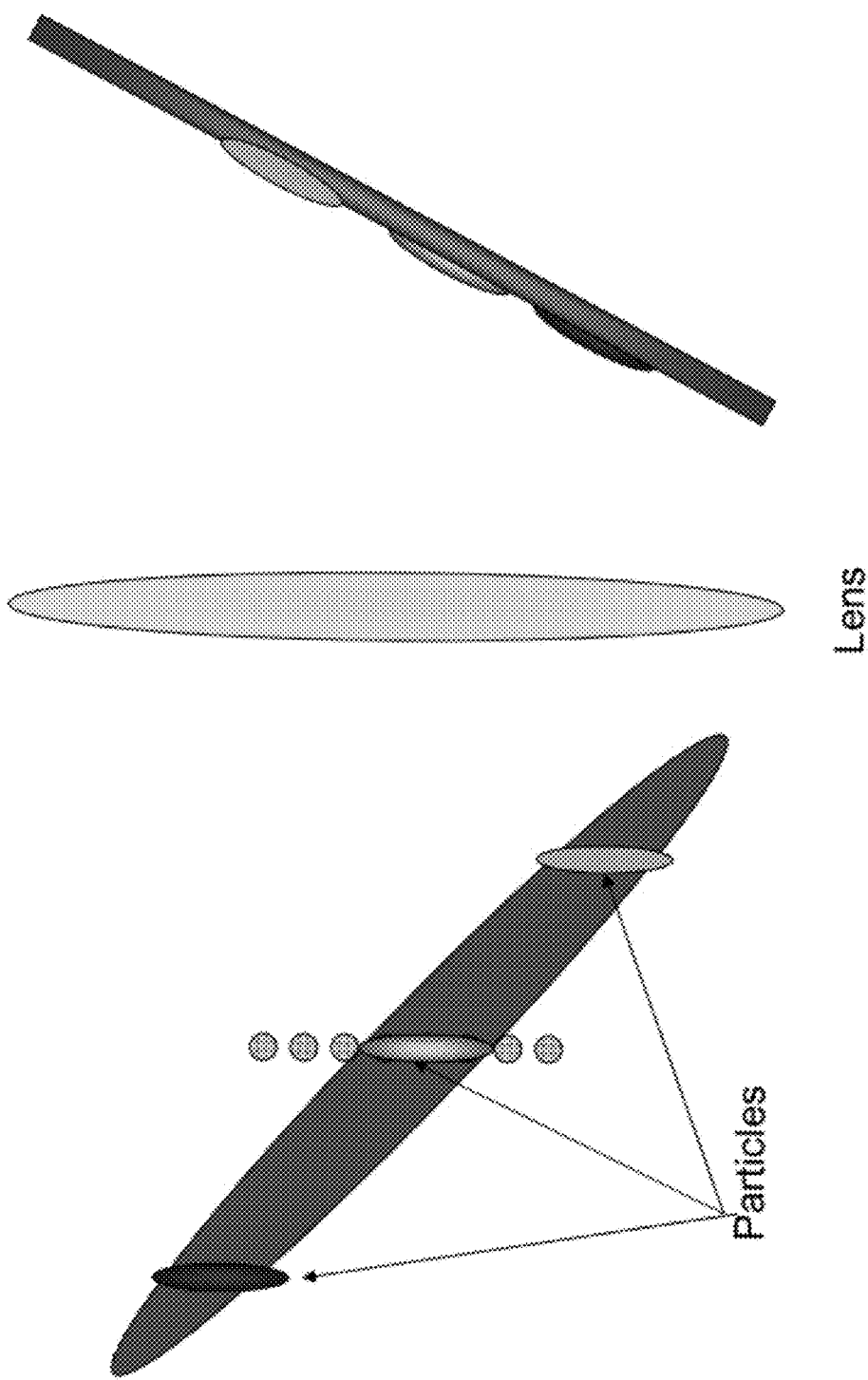
FIG. 9 shows particles passing through different spatial regions of the laser creating scattered light streaks on different spatial portions of the detector.
Figure 10:
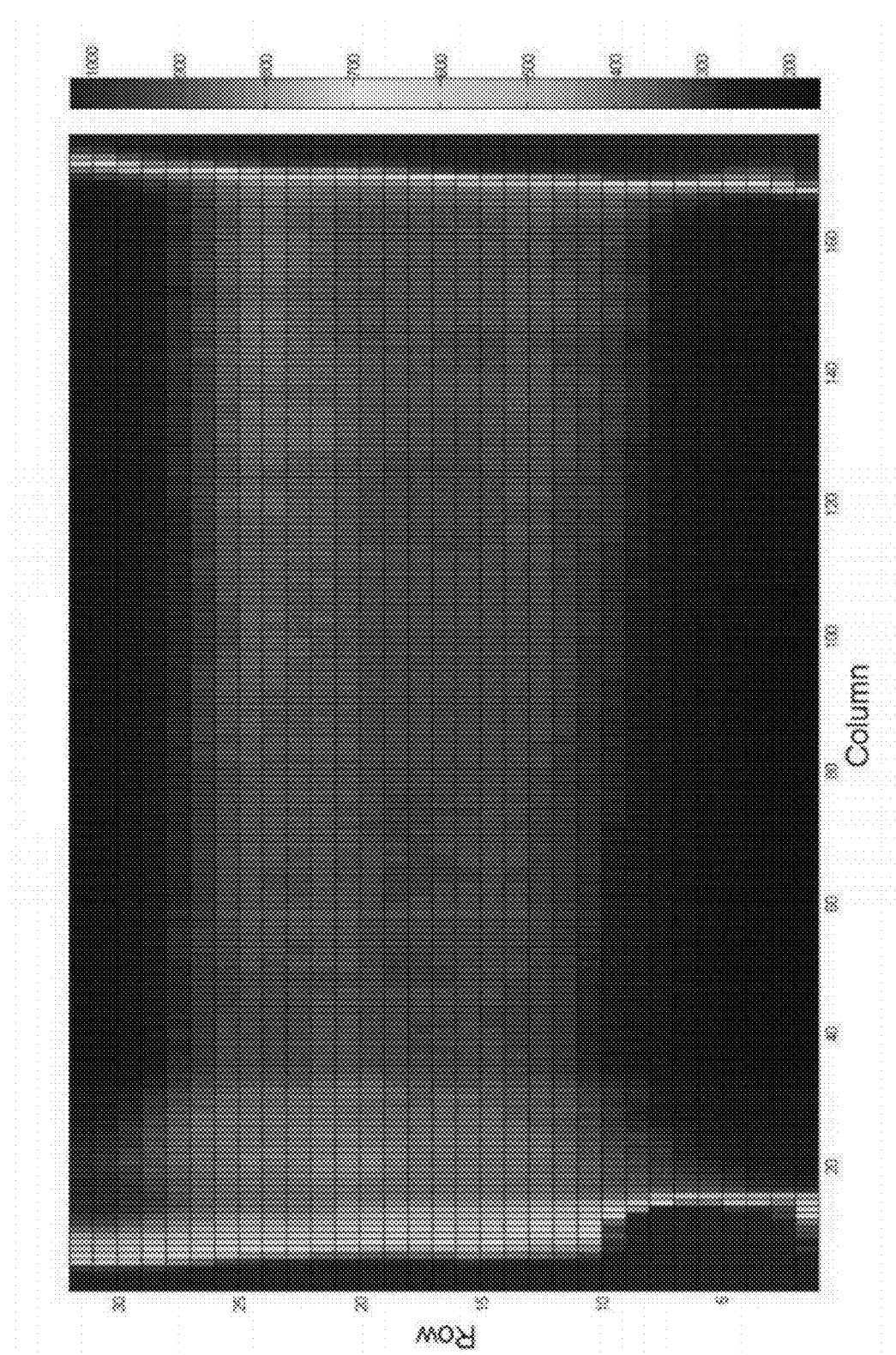
FIG. 10 provides a scattered radiation intensity image of the flow cell as viewed by the two dimensional detector array when no particles are present.
Figure 11:
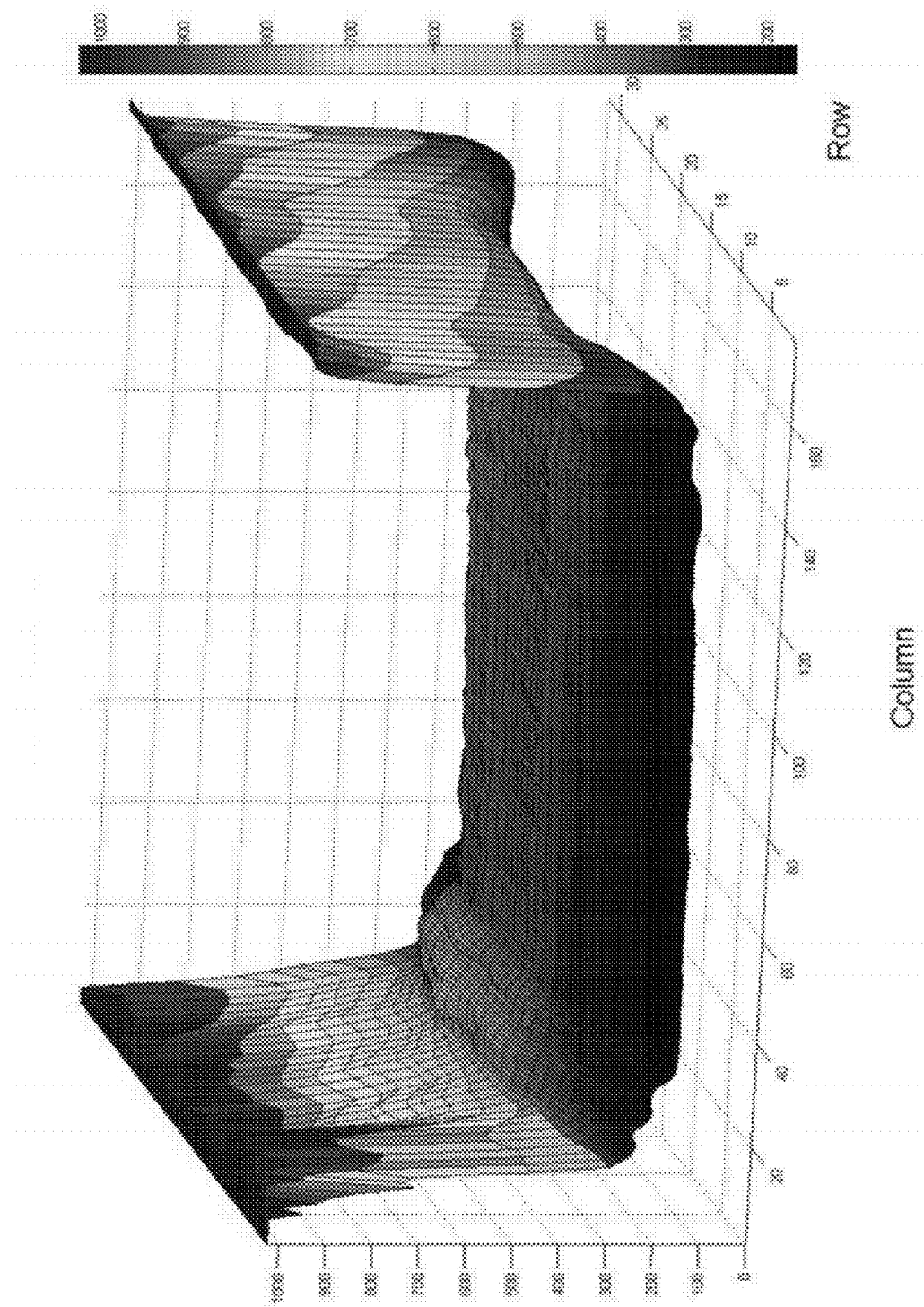
FIG. 11 provides the data from FIG. 10 as a three dimensional intensity map.

A particle passing through the laser will create a streak of scattered light on the detector, for example as shown in FIG. 8. FIG. 9 shows particles passing through different spatial regions of the laser creating scattered light streaks on different spatial portions of the detector, effectively providing a two dimensional view of the flow cell illuminated by the laser. FIG. 10 provides a scattered radiation intensity image of the flow cell as viewed by the two dimensional detector array when no particles are present, showing light scattered from the walls of the flow cell at the extremes of the image. FIG. 11 provides the data from FIG. 10 as a three dimensional intensity map.

Figure 12:
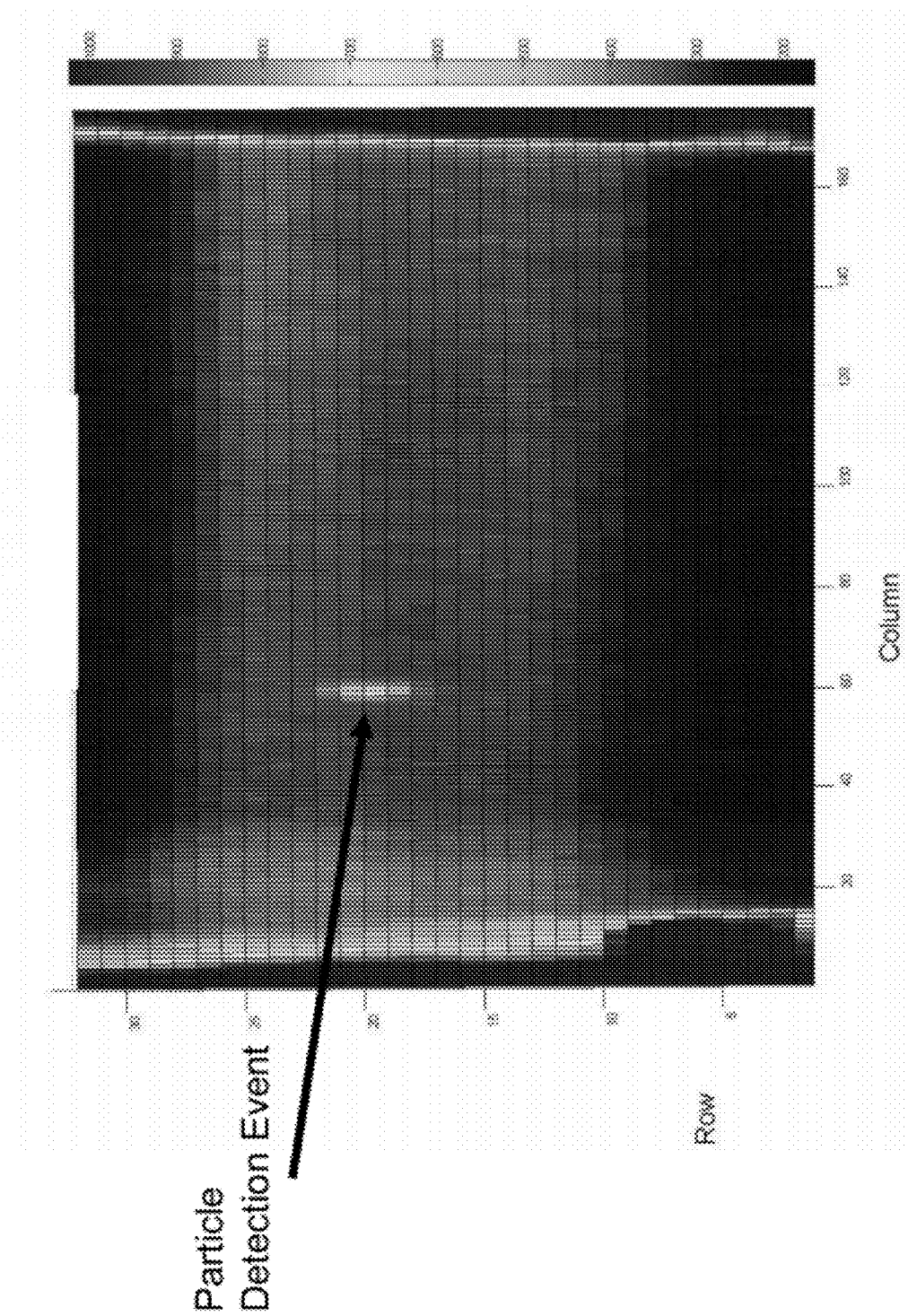
FIG. 12 provides a scattered radiation intensity image of the flow cell as viewed by the two dimensional detector array when a single particle is present.
Figure 13:
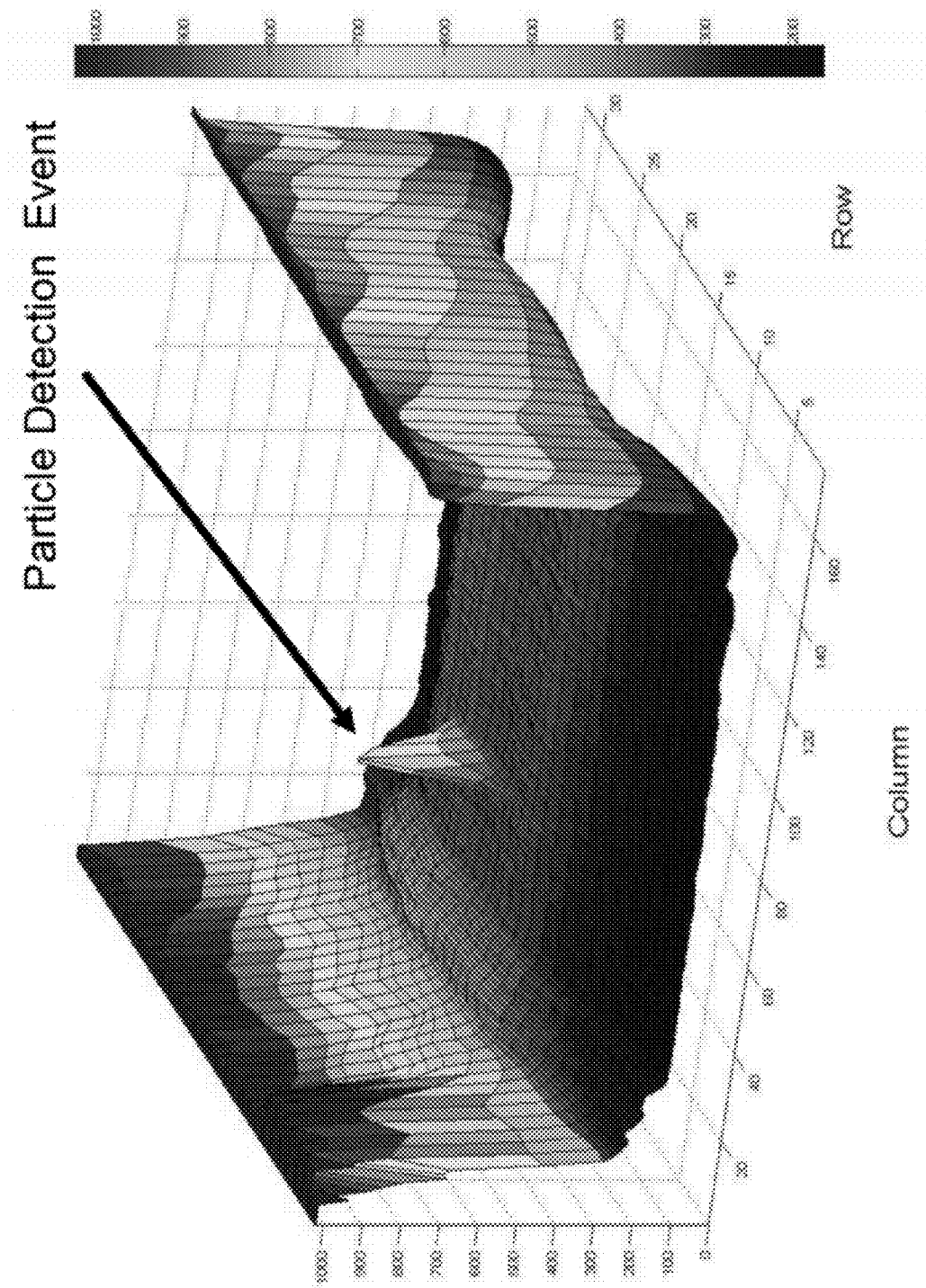
FIG. 13 shows the data from FIG. 12 as a three dimensional intensity map.
Figure 14:
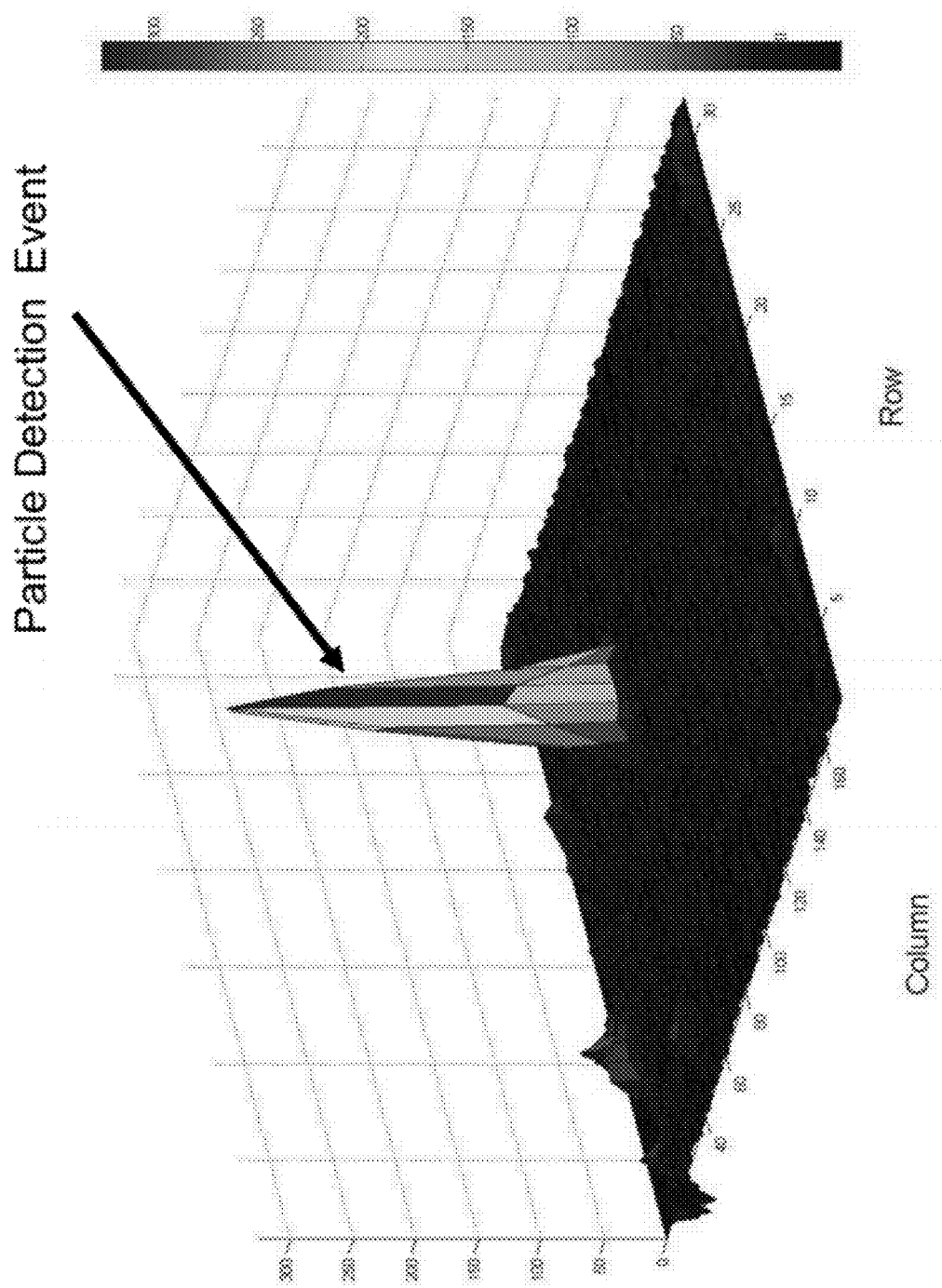
FIG. 14 shows a background subtracted image as a three dimensional intensity map.

FIG. 12 provides a scattered radiation intensity image of the flow cell as viewed by the two dimensional detector array when a single particle is present. In this image, particles are flowing through the flow cell from top to bottom, and the laser is passing through the flow cell from left to right. FIG. 13 shows the data from FIG. 12 as a three dimensional intensity map, clearly showing the particle detection event. By subtracting a background image with no particles present from the image with particles present, the signal to noise ratio of the event is dramatically increased. FIG. 14 shows such a background subtracted image as a three dimensional intensity map.

As discussed above, the present invention includes systems and methods wherein a background reference frame is subtracted from images corresponding to detection events. In some embodiments, the reference frame is an average of 50-200 individual frames, thereby representing a steady state background value for each pixel. These background values are subtracted from the detection frame (i.e., detection frame corresponding to a particle scattering event) so only the transient signals are analyzed. Subtraction of the background reference frame allows detection and sizing of very small particles, whose signals are smaller than the steady state background values. In some embodiments, the reference frame is updated continuously or at certain time intervals.

In an embodiment, for example, a fraction of the pixels in a frame are averaged over 64 frames and the new values are substituted for the reference background frame. In an embodiment, the entire reference frame is updated over 0.5-3 seconds depending on the frame rate. This aspect allows the system to compensate for changes in the extent of background scattered light, for example, due to deposition of contaminants on the walls of the optical cell or change in the optical properties of the flow cell.

Figure 15:
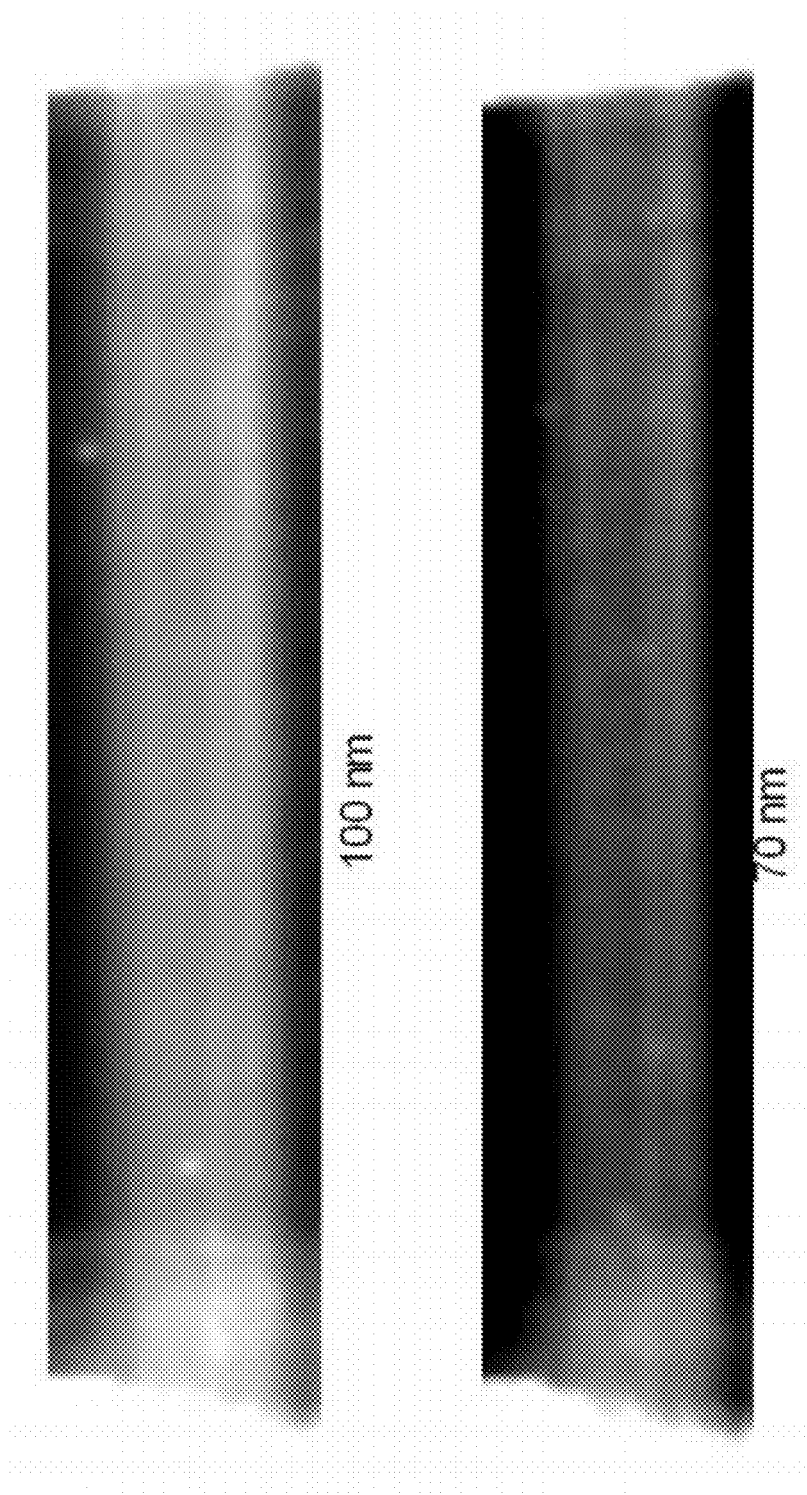
FIG. 15 provide raw (i.e., no background subtracted) scattered radiation intensity images of the flow cell as viewed by the two dimensional detector array with 100 and 70 nm particles present.
Figure 16:
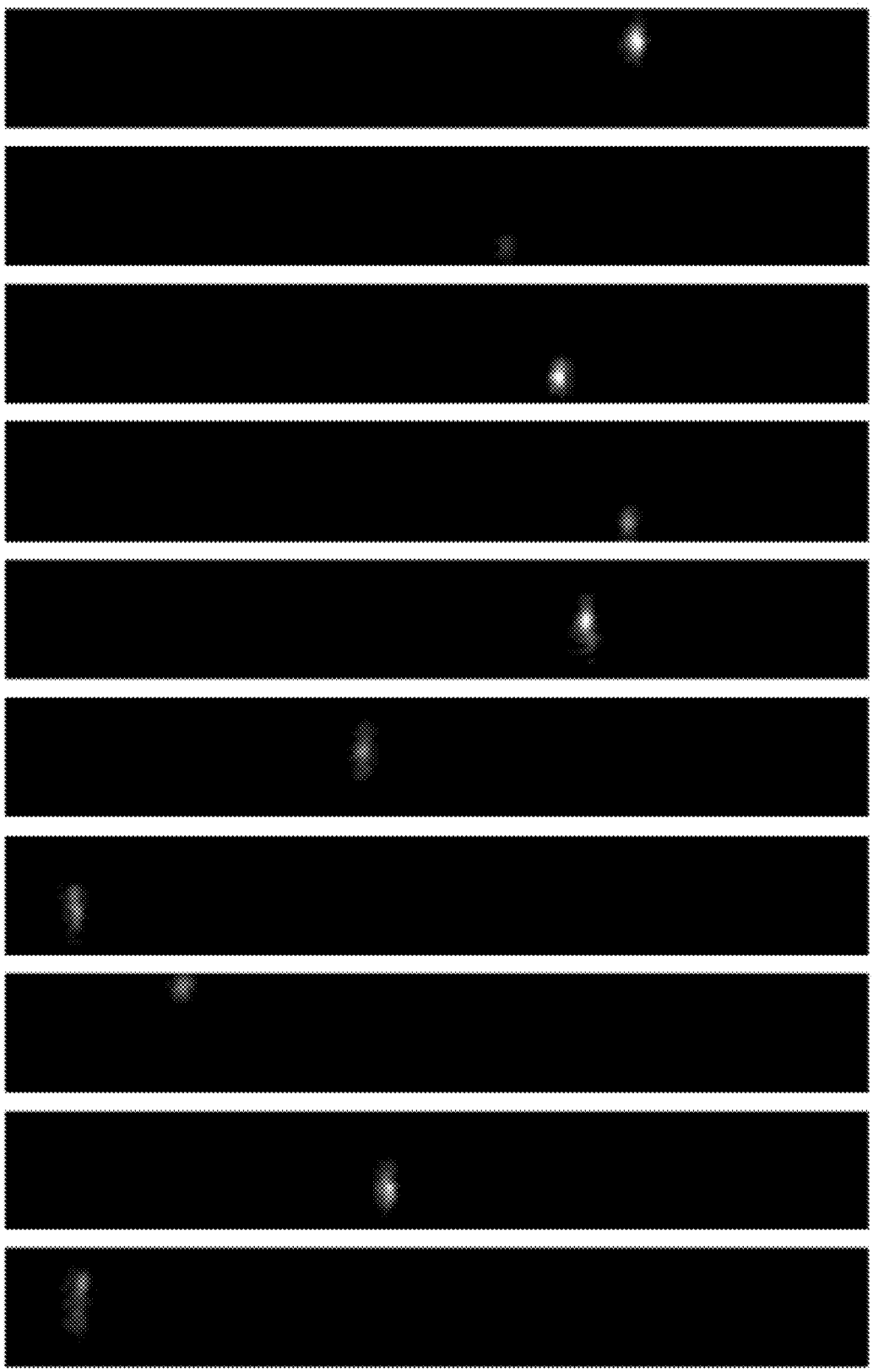
FIG. 16 provides a sequence of background subtracted scattered radiation intensity images of the flow cell as viewed by the two dimensional detector array when particles are present.

FIG. 15 provides raw (i.e., no background subtracted) scattered radiation intensity images of the flow cell as viewed by the two dimensional detector array with 100 and 70 nm particles present. FIG. 16 provides a sequence of background subtracted scattered radiation intensity images of the flow cell as measured by the two dimensional detector array when particles are present. In embodiments of the present invention, the signal from a particle is reconstructed from a plurality of two-dimensional images corresponding to the passage of the particle through the detection volume. This aspect of the present systems and methods is useful for generating a composite image of a particle detection event that can be analyzed to yield very accurate particle size information. In some embodiments, a composite image of each particle scattering event is stored and/or displayed in real time. In some embodiments, the position of the particle in the optical cell is displayed in real time. Some imaging-based optical particle counters of this aspect provide single shot display of all of the particles detected.

Figure 17:
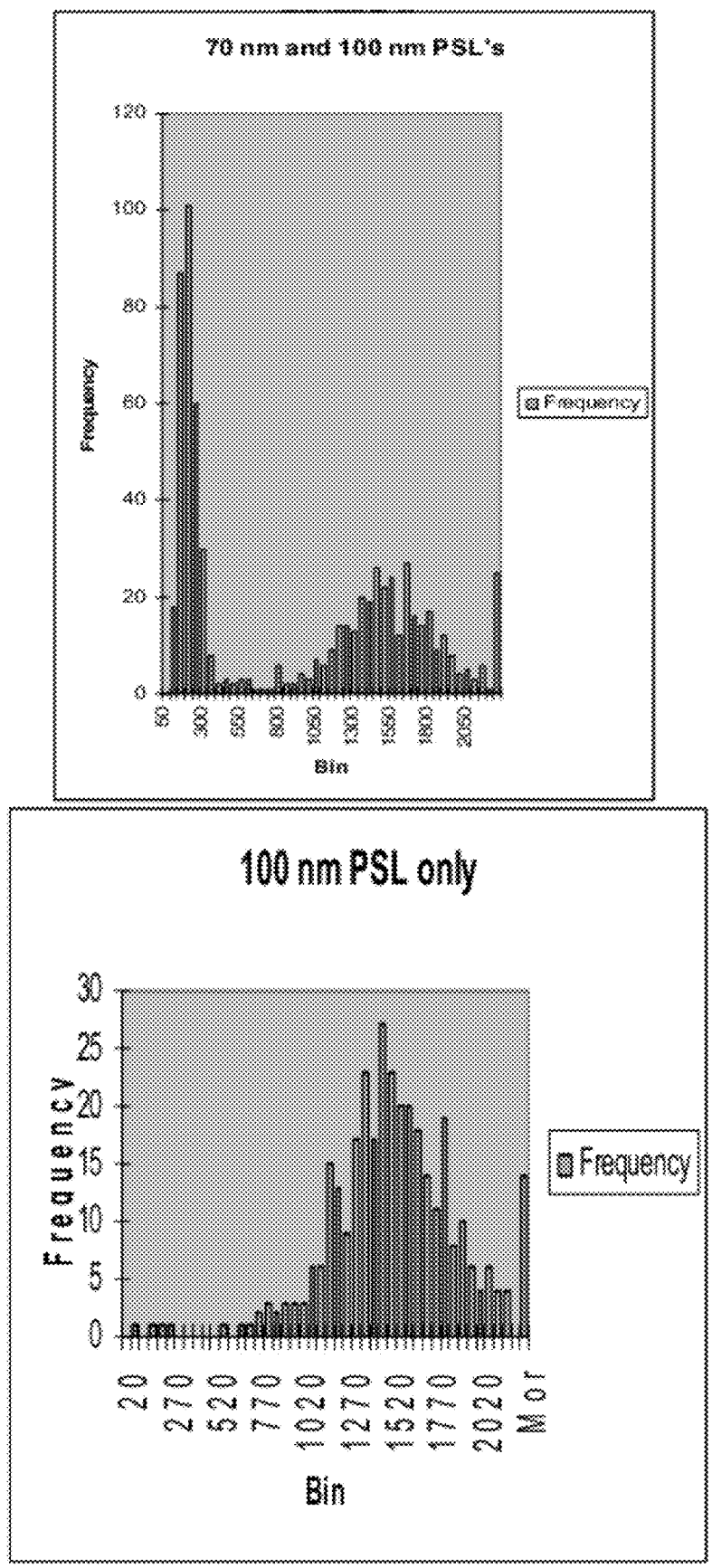
FIG. 17 shows size distributions of particles detected with 100 nm particles only (left) and both 70 and 100 nm particles present (right).
Figure 18:
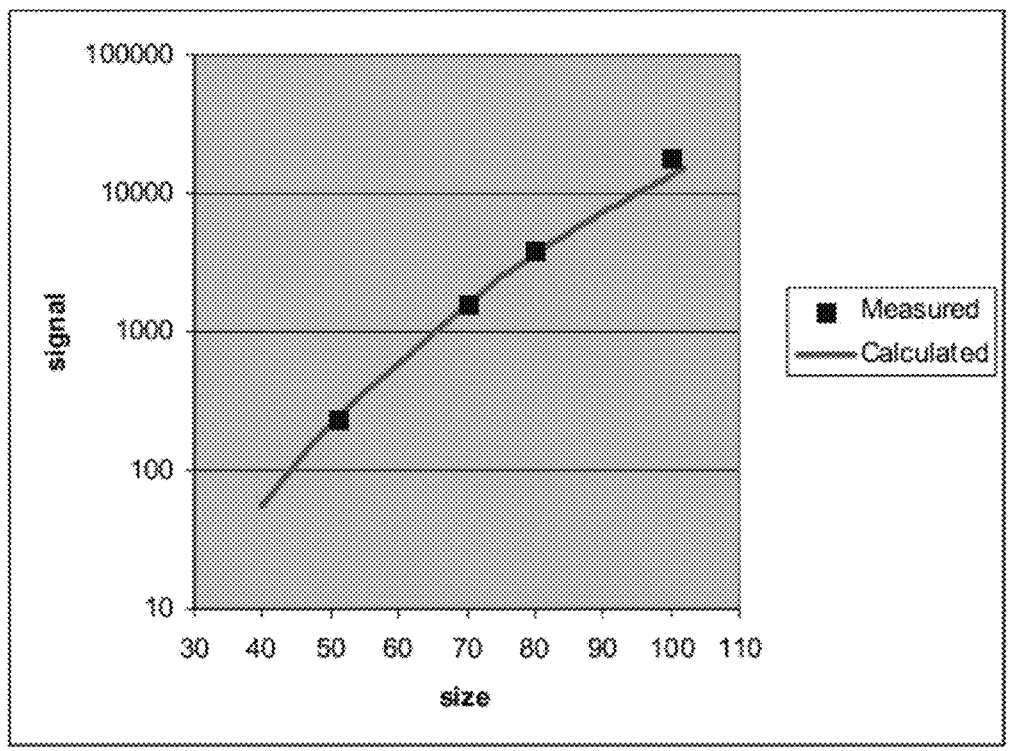
FIG. 18 provides data showing the scattered radiation signal versus particle size for particles 50, 70, 80 and 100 nm in size.
Figure 19:
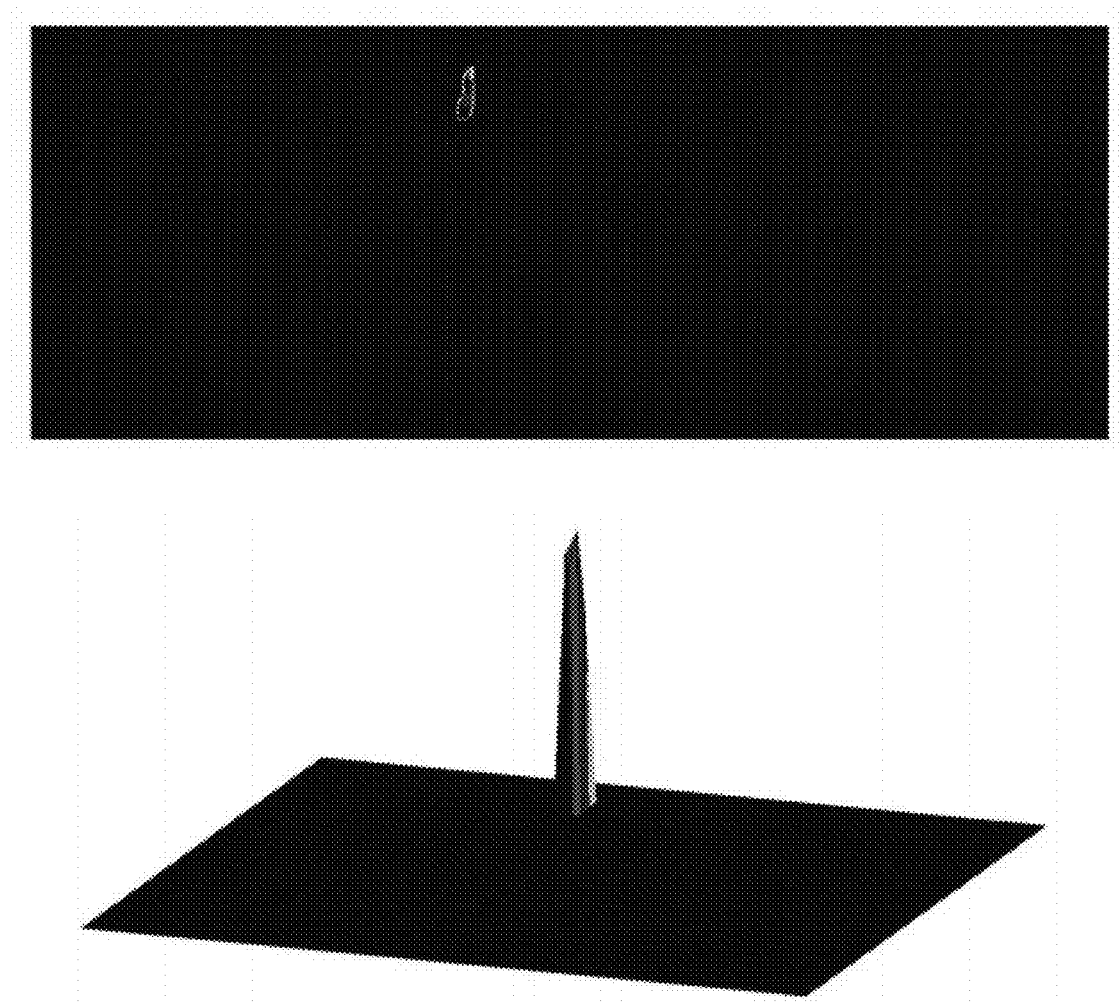
FIG. 19 provides two dimensional and three dimensional background subtracted scattered radiation intensity profiles.

FIG. 17 provides size distributions of particles detected with 100 nm particles only (left) and both 70 and 100 nm particles present (right). As the size of the particles decreases, the amount of scattered radiation from a particle detection event reaching the detector is reduced. FIG. 18 provides data showing the scattered radiation signal versus particle size for particles 50, 70, 80 and 100 nm in size, as well as a theoretical prediction of signal versus particle size. Particles as small as 40 nm are detectable using the present imaging-based optical particle counter, as shown in FIG. 18. FIG. 19 provides two dimensional and three dimensional background subtracted scattered radiation intensity profiles.

Additionally, by utilizing a higher resolution detector array, better imaging performance and sensitivity is achieved, for example by illuminating more detector elements per particle detection event. Further, by optimizing the system geometry, the detector elements can be illuminated for a longer period of time during a particle detection event, enhancing imaging performance and sensitivity. Additionally, by optimizing the optical collection system by magnifying the image of the flow cell on the two dimensional detector array, background scattered signals (and noise) can be reduced; by optimizing the focus of the image on the two dimensional detector array, a smaller particle detection event spot size can be achieved, further improving signal levels.

Particle detection systems of the present invention utilizing a two dimensional detector array provide additional enhancements, for example by providing high sample flow rates (e.g., 0.5 mL per minute or more) with high counting efficiency at small particle sizes, e.g., 30 nm or greater. In some embodiments using a CMOS sensor for optical detection, a sub-array of the sensor is used for data acquisition which can be read-out and processed very rapidly to provide a further enhancement of sensitivity. In some embodiments, limiting the detection area to a sub-array of the sensor allows measurement of particles that transit the center portion of the laser beam having substantially uniform high intensity light while preventing measurement of scattered light from particles transported through the edge of the laser beam, thereby increasing the size resolution provided by the measurement.

Imaging-based particle counters of the present invention optionally include calibration verification, for example, using reference frame comparisons, particle spot sizes or a combination of these.

EXAMPLE 2

Advanced Image Processing Methods for Optical Particle Counting

Imaging-based optical particle counters of the present invention integrate advanced image processing methods allowing for the sensitive detection and size characterization of particles at low concentrations with cross sectional dimensions as low as about 40 nanometers. This Example provides a description of certain imaging processing methods of the present invention providing enhancements relative to conventional imaging-based approaches to particle detection. Features of the present image processing methods include: (i) pixel culling wherein pixels are filtered so only those pixels that exceed a threshold value (the "threshold") and neighboring pixels are retained and analyzed to provide particle size information; (ii) generation and real time analysis of composite images from multiple frames acquired by the imaging system, wherein pixels associated with a particle detection event from a plurality of frames are combined to produce a composite image that is analyzed to provide particle size information; and (iii) use of pixel threshold values based on actual noise measurements, wherein the noise on each pixel (or optionally some larger group of pixels) is measured and the detection threshold value for that pixel is based on a predetermined multiple of the noise measurement (e.g., standard deviation of the background or multiple thereof).

FIGS. 20, 21, 22 and 23 provide flow diagrams exemplifying aspects of the image processing methods of the present invention for detecting and determining the sizes of particles in a fluid flow.

Figure 20:
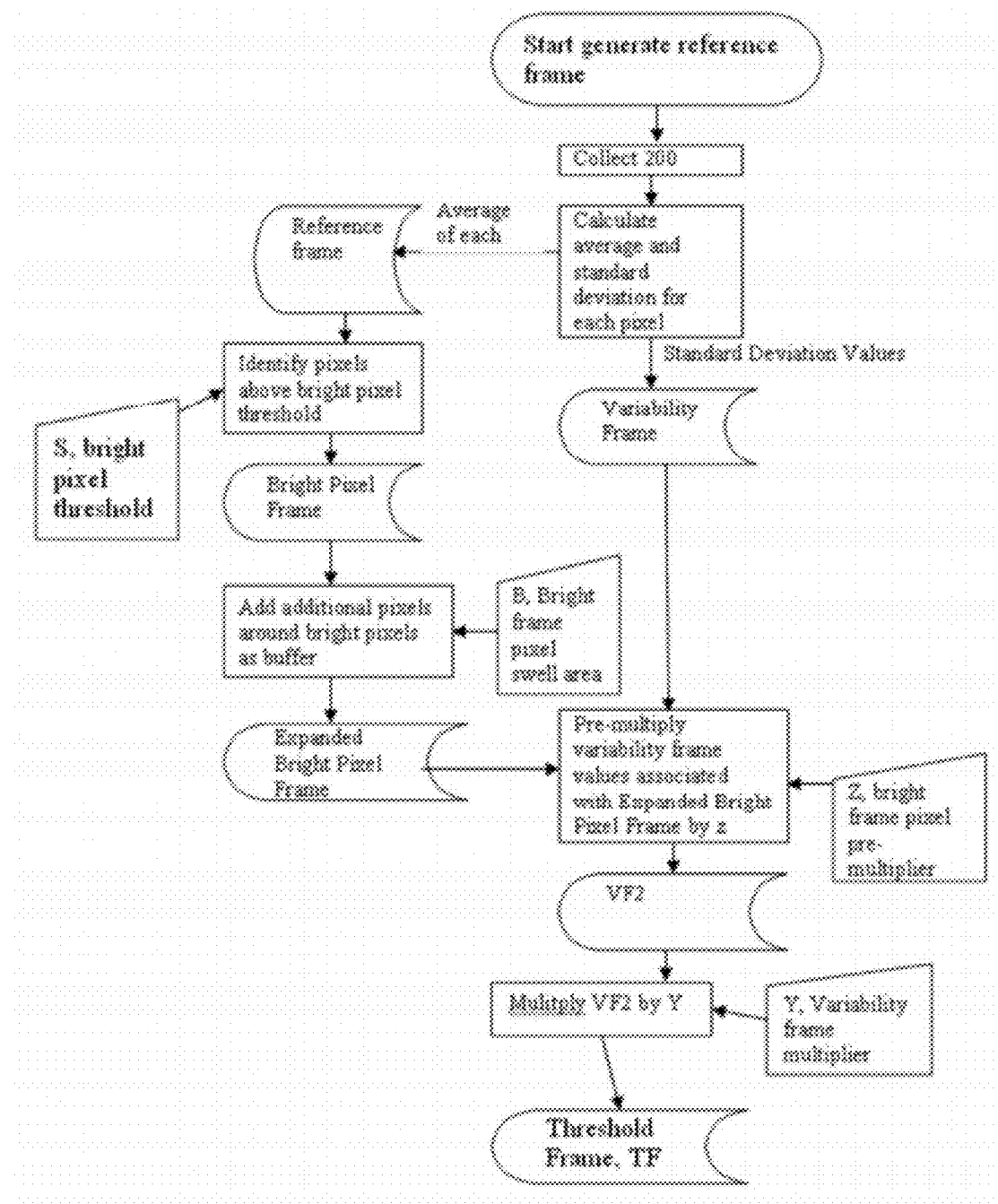
FIG. 20 provides a flow diagram exemplifying aspects of the image processing methods of the present invention for detecting and determining the sizes of particles.

The flow diagram in FIG. 20 exemplifies a process of the present invention for generating a reference frame and threshold frame. As shown in this figure, two hundred reference frames are collected and analyzed by determining the standard deviation for each pixel so as to calculate a threshold frame useful for detection and analysis of scattered electromagnetic radiation from a particle. It is important to note that the threshold values for each pixel are determined by statistical analysis on a pixel-by-pixel basis of fluctuation of the background signal in the absence of scattered light from a particle. In an embodiment, for example, a variability frame reflecting standard deviation values of the noise of the background for each individual pixel is generated and multiplied by a variable frame multiplier (Y) to determine the threshold frame. In an embodiment, the variable frame multiplier (Y) is a value selected from 2.5 to 7.

Figure 21:
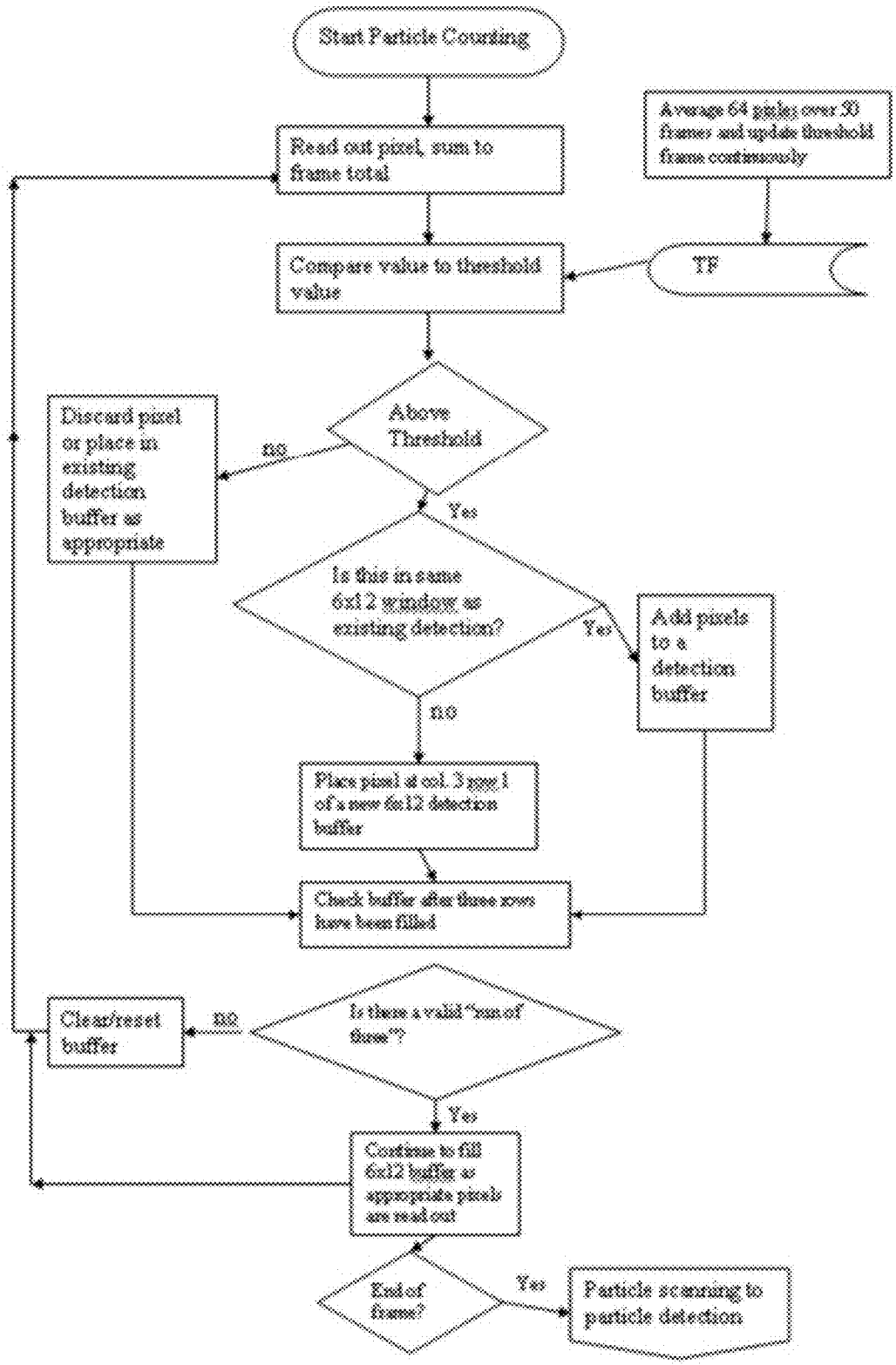
FIG. 21 provides a flow diagram exemplifying aspects of the image processing methods of the present invention for detecting and determining the sizes of particles.

FIG. 21 exemplifies a method of the present invention for counting particles wherein individual pixel values are read out and compared to threshold values. As discussed above, in the context of FIG. 20, this comparison is carried out on a pixel-by-pixel basis. If the value for a given pixel is above the threshold, the analysis algorithm determines if the pixel is in the same 4-8 by 10-14 (optionally 6 by 12) window of pixels as an existing particle detection event, and if so the pixel is added to a detection buffer. The buffer is then checked to see if there are three adjacent pixels having values above threshold. If no three adjacent pixels have values are above threshold, the buffer is cleared or reset. If three or more adjacent pixels have values above threshold, a particle detection event is identified and the buffer is continued to be filled in as appropriate pixels are read out. For example, a particle detection signature comprising at least 3 neighboring or directly neighboring pixels is used in this aspect to identify a particle detection event and to count particles.

Figure 22:
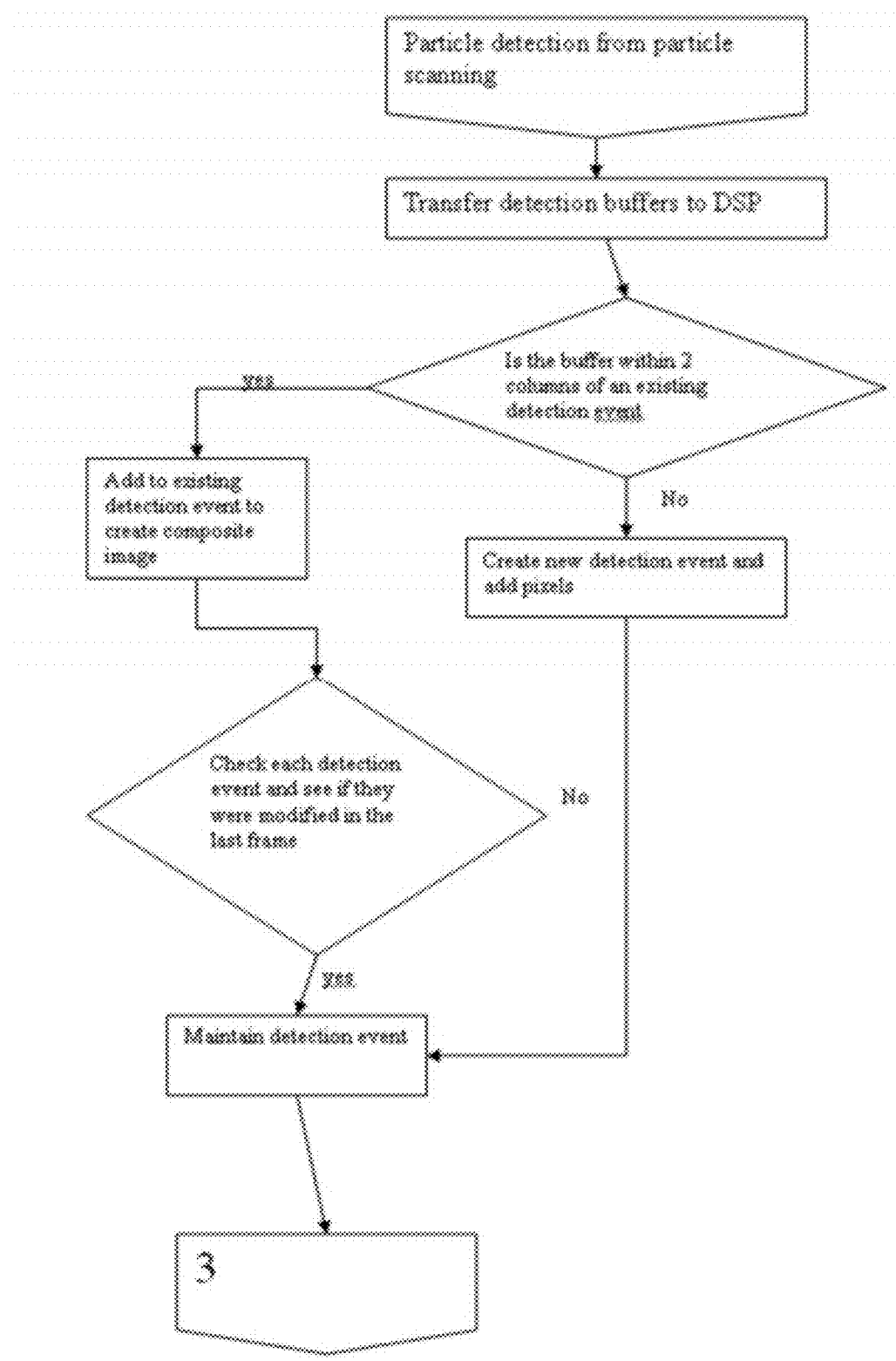
FIG. 22 provides a flow diagram exemplifying aspects of the image processing methods of the present invention for detecting and determining the sizes of particles.
Figure 23:
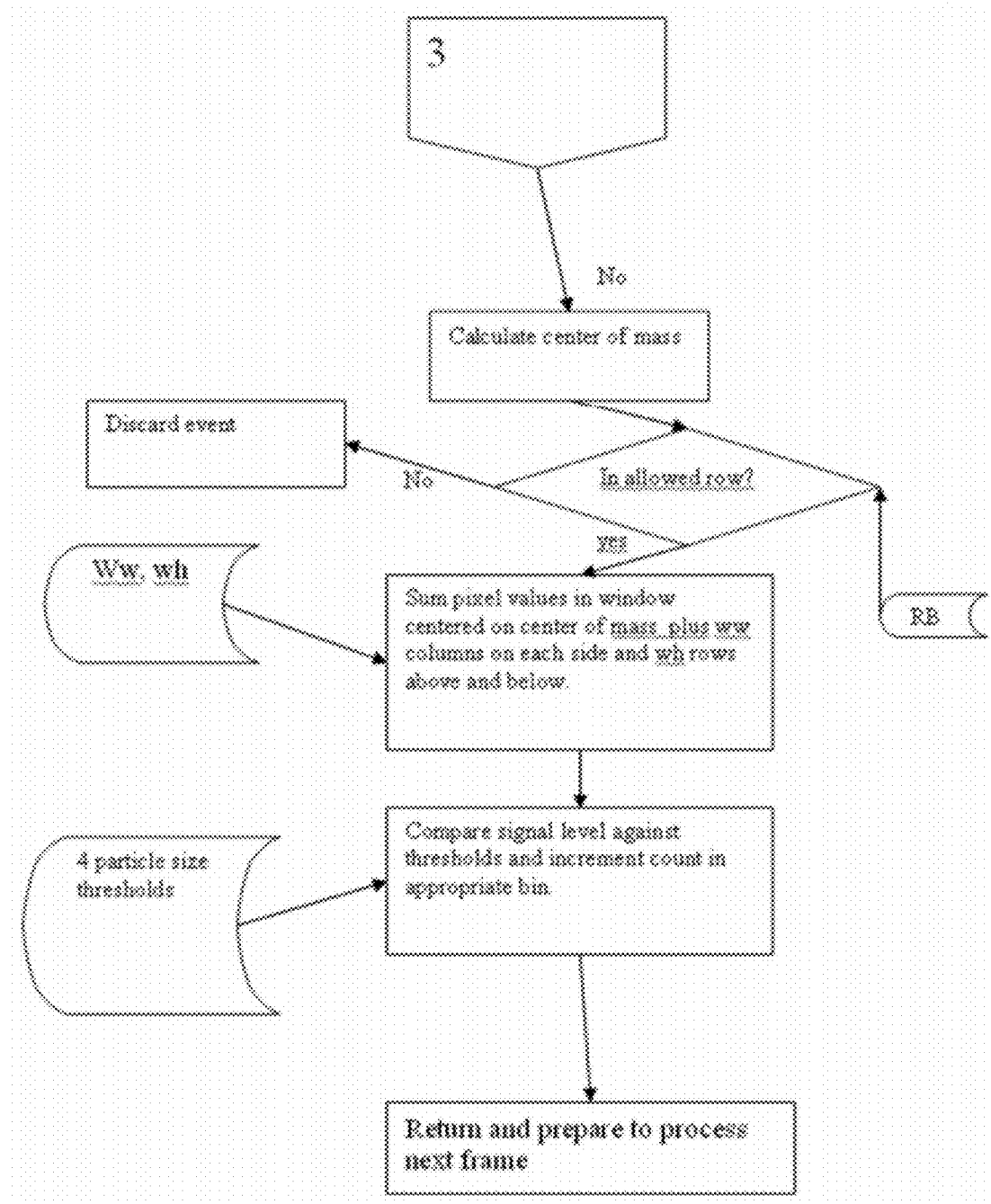
FIG. 23 provides a flow diagram exemplifying aspects of the image processing methods of the present invention for detecting and determining the sizes of particles.

FIGS. 22 and 23 exemplify methods of the present invention for determining the size of a detected particle by analysis of a particle detection signature. FIG. 22 illustrates a process for the generation of a composite image for a detection event. In an embodiment, the detection buffer is transferred to a DSP (e.g., a processor) for analysis. If the values in the buffer are within 2 columns of pixels corresponding to an existing detection event, the buffer is added to an existing detection event so as to create a composite image. If the values in the buffer are not within 2 columns of pixels of an existing detection event, the buffer is designated as a new detection event so as to create a new composite image. FIG. 23 illustrates a process for determining the size of a particle using data from the buffer, for example, provided as a composite image. First, the center of mass is calculated. As used herein, the center of mass refers to the signal weighted center of intensity values from the pixels that detect scattered electromagnetic radiation from a particle of interest. Next, an integrated intensity value corresponding to an array of pixels centered upon the weighted center of intensity values is determined, for example corresponding to an array 2-5 pixels wide and 5-9 rows long (optionally 3 pixels wide and 7 rows long). To determine the particle size, the integrated intensity value is compared to reference data, for example reference data that is empirically determined using standard particles of know physical dimensions.

The discussion that follows further describes aspects of imaging processing steps and algorithms useful in certain aspects of the present invention.

In an embodiment, the particle counter operates by imaging the laser beam passing through the flow cell onto a CMOS 2-dimensional detector array. The CMOS chip is controlled by a camera system that reads out the pixels and communicates the data to a data processing system. The camera allows sub-arrays of the chip to be defined and other areas are ignored. The sub-array of interest, or Region of Interest (ROI), is read out row by row, where each pixel from the first row is read out, then the next row, and so on until every pixel has been read out and the data transferred. The array of pixel values constitutes a frame, or image, just like an image from a digital camera or digital video camera. As soon as one row is read out, the pixels are reset and immediately begin the exposure for the next frame. In some embodiments, it is possible to set exposure times to longer than the read-out time. This is called a rolling shutter and the result is the length of the exposure time is the same for each pixel, but the actual time the top row is exposed is offset from the bottom row by about the exposure period. However, images are continuous, with essentially no dead time between exposures.

A goal of the present particle counting system is to detect and size particles as they transit the laser beam. The process for doing this is similar to a traditional analog system, but detecting and sizing are carried out in two separate steps. Step one is detecting particles, and is done by looking for pulses of light and ignoring or blocking the DC background. If the particle creates a pulse of light large enough to exceed the lowest threshold, it is detected. However, instead of having just one "first threshold" like a traditional system, a different threshold is established for each pixel.

For some embodiments, the DC level is measured by acquiring 200-500 frames and calculating the average value for each pixel. The array of average values for each pixel is called the "reference frame" and represents the DC level. In addition, the variability, or noise, of every pixel is measured as part of this process and is represented by the standard deviation of the values from the 200-500 frames. This array of standard deviation values for each pixel is called the variability frame.

There is also a "bright pixel" frame. For embodiments utilizing a CCD-based camera, it was found that pixels that imaged the bright region near the glass-water interface had values at or near their saturation levels. These pixels behaved somewhat more erratically than pixels that had values at less than half the saturation level. Therefore the pixels above a user-defined level (for example, 400-700) and some number of neighboring pixels (for example, the 2 adjacent pixels) are identified as "bright pixels" and treated differently, described below.

The values in the variability frame that correspond to the bright pixels are "pre-multiplied" by a user-defined value, creating the "modified variability frame" which is then multiplied by another factor and added to the reference frame to create the "threshold frame". For example, the pre-multiplier is 3 and the multiplier is as low as 3. Given these values, the standard deviation of the bright pixels will be multiplied by 9 and all other "normal" pixels have the standard deviation multiplied by 3. Thus, for most pixels, the value must exceed the average by 3 standard deviations in order to exceed the threshold. This multiplier value is user-configurable.

Once particle measurement starts, the threshold frame is continuously updated, for example, by taking 64 pixels and averaging them over 50 frames. The averages for these 64 pixels are then used to update the reference frame to correct for any changes in the DC level. The entire reference frame is updated about every two seconds, for example.

Measurement:

When particle counting is started, continuous "measurement" frames are collected and analyzed. The analysis consists of two distinct steps. The first step is to "detect" a particle and the second is to determine the size of the particle. Each frame is analyzed individually, but a particle takes longer to traverse the laser beam than the exposure time for a single frame. Therefore the signals from a particle may be spread over several frames and those frames can be recombined to represent the entire signal from a particle. In the present description, the recombined signal is referred to as a "composite image."

When the first measurement frame is received by the frame grabber system from the camera, each pixel value is compared against a threshold for that pixel. The first time a pixel exceeds threshold, that pixel (value and location) is placed in a detection buffer, for example, that is 6 columns wide by 12 rows high. The pixel is "centered" in column 3 of the buffer on the first row of the buffer. As pixels are read out the appropriate pixels that are located in this 6×12 window are placed in the buffer. After 3 rows are collected the buffer is checked to see if there are three vertically adjacent pixels. If yes, the buffer is allowed to continue to fill; if no, the buffer is cleared and made available for subsequent detections. At the end of the frame all buffers with valid "runs of three" are transferred to the DSP and then cleared. Subsequent frames are analyzed the same way.

When the buffers are transferred to the DSP they are checked to see if they are part of an existing detection event. If yes (same column or nearby), then the pixels are added to the event to create a composite image. If no, then a new event is created.

Next, the detection events stored in the DSP are checked to see if they were modified in a recent frame. If the event was modified then it is maintained for another frame. If not modified then the event is considered complete and the process for calculating the signal begins.

The first step in calculating the signal is to calculate the signal-weighted center of the image. The location is checked against the "rb" (subset of the ROI to allow rejection of particles near the top or bottom edges) setting to see if it is in an allowed row. Next, the appropriate pixels are identified by adding 1 column on each side of the center of mass and 3 rows above and below the center of mass to create a rectangle of 21 pixels that is 3 columns wide and 7 rows high, for example. The background-subtracted values for those 21 pixels are summed and that value is deemed the particle signal. The signal is then compared to the size thresholds and the appropriate size bin is incremented.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference). U.S. nonprovisional application entitled "Non-Orthogonal Particle Detection Systems and Methods" by John Mitchell, Jon Sandberg and Dwight A. Sehler, filed on Dec. 2, 2008 is incorporated by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method for detecting a single particle in a fluid flow, said method comprising the steps:
    providing said fluid flow having said particle;
    exposing said fluid flow to a beam of electromagnetic radiation by passing said particle in said fluid flow through said beam of electromagnetic radiation, wherein interaction between said particle and said beam of electromagnetic radiation generates scattered or emitted electromagnetic radiation from said particle;
    directing at least a portion of said scattered or emitted electromagnetic radiation from said particle onto a plurality of detector elements provided in an array of a two-dimensional detector;
    detecting at least a portion of the scattered or emitted electromagnetic radiation from said particle for a single particle detection event corresponding to passage of said particle through said beam of electromagnetic radiation, wherein at least a portion of said detector elements of said array generate output signals corresponding to detected intensities of said scattered or emitted electromagnetic radiation from said particle,
    generating a plurality of detection frames of said two-dimensional detector for said single particle detection event corresponding to a sequence of images of said particle passing through said beam of electromagnetic radiation; wherein each detection frame comprises a plurality of said output signals of at least a portion of said detector elements of said two-dimensional detector for a given time interval; wherein said time interval of each of said detection frames is less than the time it takes for the particle to traverse said beam of electromagnetic radiation;
    combining a plurality of said detection frames to provide a composite image of a said single particle detection event;
    wherein said composite image comprises a composite of data points resulting from a combination of at least a portion of the output signals for said plurality of detection frames for said single particle detection event;
    analyzing said composite image to determine a size of the particle, thereby detecting said particle.

2. The method of claim 1 further comprising identifying said detection frames having output signals corresponding to detected intensities of electromagnetic radiation scattered or emitted from said particle.

3. The method of claim 1 wherein said detection frames are generated at a rate of 0.1 kHz to 20 kHz.

4. The method of claim 1 wherein each detection frame corresponds to a time interval of 50 μs to 10 ms.

5. The method of claim 1 wherein 2 to 100 detection frames are combined to generate the composite image.

6. The method of claim 1 further comprising the step of subtracting a reference frame from each of said detection frames; wherein the reference frame comprises background output signals for the detector elements in said array; wherein each background output signal is the average output signal for a given detector element in said array for detection conditions in the absence of electromagnetic radiation scattered or emitted from said particle.

7. The method of claim 6 wherein the reference frame is continuously updated.

8. The method of claim 6 wherein the reference frame is an average of 50 to 200 individual frames.

9. The method of claim 1 further comprising the step of imaging at least a portion of the scattered or emitted electromagnetic radiation from said particle onto said detector elements of said array of said two-dimensional detector.

10. The method of claim 1 wherein said detection frames correspond to images of said particle in said fluid flow.

11. The method of claim 1 wherein each of said detection frames comprises a plurality of said output signals of a subset of said detector elements of said two-dimensional detector.

12. The method of claim 1 wherein each of said detection frames comprises a plurality of said output signals of a sub-array of said two-dimensional detector.

13. The method of claim 12 wherein the sub-array comprises 0.2% to 25% of the detector elements of the two-dimensional detector.

14. The method of claim 1 wherein said step of analyzing said composite image comprises calculating a signal-weighted center of intensity value of the composite image.

15. The method of claim 14 wherein said step of analyzing said composite image further comprises determining an integrated intensity value corresponding to output values of an array of detector elements centered upon said signal-weighted center of intensity value.

16. The method of claim 15 wherein said array of detector elements centered upon said signal-weighted center of intensity value is 2-5 detector elements wide and 5-9 detector elements long.

17. The method of claim 15 wherein said step of analyzing said composite image further comprises comparing said integrated intensity value to reference data to determine said size of the particle.

18. The method of claim 17 wherein said reference data is determined using particles of known physical dimensions.

19. The method of claim 1 further comprising the step of collecting at least a portion of said scattered or emitted electromagnetic radiation from said particle.

20. The method of claim 1 wherein said two-dimensional detector is a two-dimensional array of photodetectors, a charge-coupled device (CCD) detector, a complementary metal-oxide-semiconductor (CMOS) detector, a metal-oxide-semiconductor (MOS) detector, an active pixel sensor, a microchannel plate detector, a two-dimensional array of photomultiplier tubes, a two-dimensional array of photodiodes, a two-dimensional array of phototransistors, a two-dimensional array of photoresistors, or a photoconductive film.

21. The method of claim 1 wherein the fluid flow is a flow of liquid containing said particle.

22. The method of claim 1 wherein the fluid flow is a flow of water containing said particle.

23. The method of claim 1 wherein the fluid flow is a flow of gas containing said particle.

24. The method of claim 1 further comprising the steps of:
determining a subset of said detector elements of said array, said subset comprising a plurality of detector elements, wherein each detector element of said subset has an output signal greater than or equal to a threshold value for a given detector element;
transmitting to a processor only the output signals of said subset.

25. The method of claim 24 wherein said subset comprises 2 to 10 detector elements of said array.

26. The method of claim 1 further comprising the steps of:
detecting at least a portion of said scattered or emitted electromagnetic radiation using a sub-array of said two-dimensional detector, wherein at least a portion of said detector elements of said sub-array generate output signals corresponding to intensities of said scattered or emitted electromagnetic radiation;
transmitting to a processor only output signals of said detector elements corresponding to said sub-array or a portion thereof.

27. The method of claim 26 wherein the sub-array comprises 0.2% to 25% of the detector elements of the two-dimensional detector.

28. The method of claim 26 wherein the sub-array comprises 1000 to 100000 detection elements.

* * * * *

UNITED STATES PATENT AND TRADEMARK OFFICE
CERTIFICATE OF CORRECTION

| | | |
|---|---|---|
| PATENT NO. | : 8,427,642 B2 | Page 1 of 1 |
| APPLICATION NO. | : 13/396393 | |
| DATED | : April 23, 2013 | |
| INVENTOR(S) | : John Mitchell et al. | |

It is certified that error appears in the above-identified patent and that said Letters Patent is hereby corrected as shown below:

In the Claims

In claim 1, column 32, line 8, replace "of a said single" with --of said single--.

Signed and Sealed this
Seventeenth Day of June, 2014

Michelle K. Lee
*Deputy Director of the United States Patent and Trademark Office*